US008093009B2

(12) United States Patent
Halperin

(10) Patent No.: US 8,093,009 B2
(45) Date of Patent: Jan. 10, 2012

(54) MASS SPECTROMETRIC METHODS AND PRODUCTS

(75) Inventor: Jose Halperin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/917,271

(22) Filed: Nov. 1, 2010

(65) Prior Publication Data

US 2011/0053177 A1      Mar. 3, 2011

Related U.S. Application Data

(62) Division of application No. 11/794,635, filed as application No. PCT/US2006/000310 on Jan. 6, 2006, now Pat. No. 7,833,725.

(60) Provisional application No. 60/641,762, filed on Jan. 6, 2005.

(51) Int. Cl.
*G01N 33/53* (2006.01)

(52) U.S. Cl. .......................................... 435/7.1; 436/518

(58) Field of Classification Search ........................ None
See application file for complete search history.

(56) References Cited

U.S. PATENT DOCUMENTS

| | | | |
|---|---|---|---|
| 4,281,061 A | 7/1981 | Zuk et al. | |
| 4,816,567 A | 3/1989 | Cabilly et al. | |
| 5,225,539 A | 7/1993 | Winter | |
| 5,470,759 A | 11/1995 | Sugiyama et al. | |
| 5,585,089 A | 12/1996 | Queen et al. | |
| 5,693,762 A | 12/1997 | Queen et al. | |
| 5,789,208 A | 8/1998 | Sharon | |
| 5,853,703 A | 12/1998 | Cerami et al. | |
| 5,859,205 A | 1/1999 | Adair et al. | |
| 6,835,545 B2 | 12/2004 | Halperin | |
| 7,049,082 B2 | 5/2006 | Halperin | |
| 7,439,330 B2 | 10/2008 | Halperin | |
| 7,501,286 B2 * | 3/2009 | Gygi et al. | 436/173 |
| 7,767,791 B2 | 8/2010 | Halperin | |
| 7,833,725 B2 | 11/2010 | Halperin | |
| 2004/0119010 A1 | 6/2004 | Perryman | |
| 2004/0219606 A1 | 11/2004 | Halperin | |
| 2005/0032128 A1 | 2/2005 | Halperin | |
| 2006/0257936 A1 | 11/2006 | Halperin | |
| 2009/0191574 A1 | 7/2009 | Halperin | |
| 2010/0112708 A1 | 5/2010 | Pappin | |

FOREIGN PATENT DOCUMENTS

| | | |
|---|---|---|
| EP | 0394035 A2 | 10/1990 |
| EP | 1789449 A1 | 5/2007 |
| WO | 88/06798 A1 | 9/1988 |
| WO | 89/06798 A1 | 7/1989 |
| WO | 90/06516 A1 | 6/1990 |
| WO | 97/49429 A1 | 12/1997 |
| WO | 98/19711 A1 | 5/1998 |
| WO | 99/22242 A2 | 5/1999 |
| WO | 02/04638 | 1/2002 |
| WO | 2004/106941 A2 | 12/2004 |
| WO | WO 2004106941 * | 12/2004 |
| WO | 2006/009533 A1 | 1/2006 |
| WO | 2006/086098 A2 | 8/2006 |
| WO | 2010/002278 A1 | 1/2010 |

OTHER PUBLICATIONS

Desiderio et al.. J. Chrom. 1999 VOl. 731 B, p. 3-22.*
GENBANK Submission; NIH/NCBI, Accession No. M95708; Davies et al.
Acosta et al., Complement and complement regulatory proteins as potential molecular targets for vascular diseases. Current Pharmaceutical Design, 2004;10:1-9.
Acosta et al.,, Molecular basis for a link between complement and the vascular complications of diabetes. Proc Natl Acad Sci U S A. May 9, 2000;97(10):5450-5.
Baerga-Ortiz et al., Epitope mapping of a monoclonal antibody against human thrombin by H/D-exchange mass spectrometry reveals selection of a diverse sequence in a highly conserved protein. Protein Sci. Jun. 2002;11(6):1300-8.
Benzaquen et al.,, Terminal complement proteins C5b-9 release basic fibroblast growth factor and platelet-derived growth factor from endothelial cells. J Exp Med. Mar. 1, 1994;179(3):985-92.
Bird et al., Single-chain antigen-binding proteins. Science. Oct. 21, 1988;242(4877):423-6.
Bodian et al.,, Mutational analysis of the active site and antibody epitopes of the complement-inhibitory glycoprotein, CD59. J Exp Med. Feb. 3, 1997;185(3):507-16.
Bunn et al., Further identification of the nature and linkage of the carbohydrate in hemoglobin A1c. Biochem Biophys Res Commun. Nov. 3, 1975;67(1):103-9.
Carganico et al., Building blocks for the synthesis of post-translationally modified glycated peptides and proteins. J Pept Sci. Feb. 2009;15(2):67-71.
Davies et al., CD59, an LY-6-like protein expressed in human lymphoid cells, regulates the action of the complement membrane attack complex on homologous cells. J Exp Med. Sep. 1, 1989;170(3):637-54.
Darlak et al., Facile preparation of disulfide-bridged peptides using the polymer-supported oxidant CLEAR-OX. J Pept Res. Mar. 2004;63(3):303-12.
Falk et al., Ultrastructural localization of the membrane attack complex of complement in human renal tissues. Am J Kidney Dis. Feb. 1987;9(2):121-8.
Fletcher et al., Structure of a soluble, glycosylated form of the human complement regulatory protein CD59. Structure. Mar 15, 1994;2(3):185-99.
Halperin et al., Transient changes in erythrocyte membrane permeability are induced by sublytic amounts of the complement membrane attack complex (C5b-9). Blood. Jan. 1, 1993;81(1):200-5.
Halperin et al., Properties of the Na+-K+ pump in human red cells with increased number of pump sites. J Clin Invest. Jul. 1987;80(1):128-37.

(Continued)

*Primary Examiner* — Jacob Cheu
(74) *Attorney, Agent, or Firm* — Wolf, Greenfield & Sacks, P.C.; C. Hunter Baker

(57) ABSTRACT

The invention involves assays, diagnostics, kits, and assay components for mass spectrometry and other methods to determine levels of glycated CD59 in subjects.

11 Claims, 3 Drawing Sheets

OTHER PUBLICATIONS

Halperin et al., Terminal complement complex C5b-9 stimulates mitogenesis in 3T3 cells. J Clin Invest. May 1993;91(5):1974-8.
Harlow et al., Antibodies: A Laboratory Manual. 1998;321-323.
Hughes et al., Isolation and characterization of a membrane protein from rat erythrocytes which inhibits lysis by the membrane attack complex of rat complement. Biochem J. May 15, 1992;284 (Pt 1):169-76.
Huston et al., Protein engineering of antibody binding sites: recovery of specific activity in an antidigoxin single-chain Fv analogue produced in *Escherichia coli*. Proc Natl Acad Sci U S A. Aug. 1988;85(16):5879-83.
Kaiser et al., Color test for detection of free terminal amino groups in the solid-phase synthesis of peptides. Anal Biochem. Apr. 1970;34(2):595-8.
Kim et al., Multiple sclerosis: An important role for post-translational modifications of myelin basic protein in pathogenesis. Mol Cell Proteomics. Jul. 2003;2(7):453-62.
Koenig et al., Structure of carbohydrate of hemoglobin AIc. J Biol Chem. May 10, 1977;252(9):2992-7.
Köhler et al., Continuous cultures of fused cells secreting antibody of predefined specificity. Nature. Aug 7, 1975;256(5517):495-7.
Köhler et al., Derivation of specific antibody-producing tissue culture and tumor lines by cell fusion. Eur J Immunol. Jul. 1976;6(7):511-9.
Johansen et al., Analysis and prediction of mammalian protein glycation. Glycobiology. Sep. 2006;16(9):844-53.
Lapolla et al., The role of mass spectrometry in the study of non-enzymatic protein glycation in diabetes. Mass Spectrom Rev. Sep.-Oct. 2000;19(5):279-304. Review.
Monnier et al., Non-enzymatic glycosylation and browning of proteins in diabetes. Clin Endocrinol Metab. Jul. 1982;11(2):431-52.
Monnier et al., Maillard reaction in food and nutrition. Waller, G.A., ed. American Chemical Society. 1983:431-48.
Myint et al., Immunological detection of glycated proteins in normal and streptozotocin-induced diabetic rats using anti hexitol-lysine IgG. Biochim Biophys Acta. Oct. 17, 1995;1272(2):73-9.
Nakou et al., Gene network analysis of bone marrow mononuclear cells reveals activation of multiple kinase pathways in human systemic lupus erythematosus. PLoS One. Oct. 14, 2010;5(10):e13351.
Ninomiya et al., Contribution of the N-linked carbohydrate of erythrocyte antigen CD59 to its complement-inhibitory activity. J Biol Chem. Apr. 25, 1992;267(12):8404-10.
Ordóñez et al., Increased levels of citrullinated antithrombin in plasma of patients with rheumatoid arthritis and colorectal adenocarcinoma determined by a newly developed Elisa using a specific monoclonal antibody. Thromb Haemost. Dec. 2010;104(6):1143-9.
Philbrick et al., The CD59 antigen is a structural homologue of murine Ly-6 antigens but lacks interferon inducibility. Eur J Immunol. Jan. 1990;20(1):87-92.
Qin et al., Genomic structure, functional comparison, and tissue distribution of mouse Cd59a and Cd59b. Mamm Genome, Aug. 2001;12(8):582-9.
Qin et al., A role of glycated human CD59 and the complement system in the pathogenesis of chronic vascular complications of diabetes. Elsevier. Aug. 2002;2(9):1382-3.
Rosoklija et al., Local activation of the complement system in endoneurial microvessels of diabetic neuropathy. Acta Neuropathol. Jan. 2000;99(1):55-62.
Suzuki et al., Immunofluorescene staining of renal biopsy samples in patients with diabetic nephropathy in non-insulin-dependent diabetes mellitus using monoclonal antibody to reduced glycated lysine. J Diabetes Complications. Nov.-Dec. 1996;10(6):314-9.
Takata et al., Glycated Cu,Zn-superoxide dismutase in rat lenses: evidence for the presence of fragmentation in vivo. Biochem Biophys Res Commun. Feb. 6, 1996;219(1):243-8.
Van Den Berg et al., The sheep analogue of human CD59: purificationa nd characterization of its complement inhibitory activity. Immunology. Mar. 1993;78(3):349-57.
Wagner et al., Induction of matrix protein syntheisis in human glomerular mesangial cells by the terminal complement complex. Exp Nephrol. Jan.-Feb. 1994;2(1):51-6.
Walton et al., Synthesis on N-(1-deoxyhexitol-1-yl)amino acids, reference compounds for the nonenzymic glocosylation of proteins. Carbohydr Res. May 15, 1984;128(1):37-49.
Ward et al., Binding activities of a repertoire of single immunoglobulin variable domains secreted from *Escherichia coli*. Nature. Oct. 12, 1989;341(6242):544-6.
Weiss et al., Immunofluorescent characteristics of the diabetic cornea. Cornea. Apr. 1990;9(2):131-8.
Wilen et al., Strategies in optical resolutions. Tetrahedron. 1971;33(21):272-36.
Wilen, Tables of Resolving Agents and Optical Resolutions. Notre Dame Press. 1972:268.
Yu et al., Mapping the active site of CD59. J Exp Med. Feb. 17, 1997;185(4):745-53.
Zhang et al., Early complement activation and decreased levels of glycosylphosphatidylinositol-anchored complement inhibitors in human and experimental diabetic retinophty. Diabetes. Dec. 2002;51(12):3499-504.
Zhao et al., Amplified gene expression in CD59-transfected Chinese hamster overy cells confers protection against the membrane attack complex of human complement. J. Biol. Chem. 266: 13418-13422, 1991.
Extended European Search Report mailed Jun. 1, 2011 in connection with application No. EP 10185729.0.
Extended European Search Report mailed May 27, 2011 in connection with application No. EP 10185831.4.
International Search Report mailed Jun. 6, 2005 in connection with application No. PCT/US2004/019392.
International Preliminary Report on Patentability mailed Dec. 20, 2006 in connection with application No. PCT/US2004/019392.
Invitation ot Pay Additional Fees mailed Jul. 11, 2006 in connection with application No. PCT/US2006/000310.
International Search Report and Written Opinin mailed Oct. 30, 2006 in connection with application No. PCT/US2006/000310.
International Preliminary Report on Patentability mailed Jul. 19, 2007 in connection with application No. PCT/US2006/000310.
International Search Report and Written Opinion mailed Aug. 27, 2008 in connection with application No. PCT/U52008/005831.
International Preliminary Report on Patentability mailed Nov. 19, 2009 in connection with application No. PCT/US2008/005831.
Office Action, mailed Dec. 15, 2010, for U.S. Appl. No. 12/244,851.
Reply to Office Action, mailed Mar. 11, 2011, for U.S. Appl. No. 12/244,851.
Notice of Allowance, mailed May 16, 2011, for U.S. Appl. No. 12/244,851.
Notice of Allowance, mailed Jun. 16, 2008, for U.S. Appl. No. 11/413,130.
Reply to Office Action, mailed Jan. 16, 2008, for U.S. Appl. No. 11/413,130.
Office Action, mailed Jul. 17, 2007, for U.S. Appl. No. 11/413,130.
Reply to Office Action, mailed Dec. 7, 2006, for U.S. Appl. No. 11/413,130.
Office Action, mailed Oct. 5, 2006, for U.S. Appl. No. 11/413,130.
Reply to Office Action, mailed Sep. 26, 2005, for U.S. Appl. No. 10/833,581.
Office Action, mailed Mar. 24, 2005, for U.S. Appl. No. 10/833,581.
Reply to Office Action, mailed Oct. 20, 2003, for U.S. Appl. No. 09/835,752.
Office Action, mailed Oct. 3, 2003, for U.S. Appl. No. 09/835,752.
Reply to Office Action, mailed Jul. 11, 2003, for U.S. Appl. No. 09/835,752.
Office Action, mailed Jun. 13, 2003, for U.S. Appl. No. 09/835,752.
Reply to Office Action, mailed Mar. 19, 2003, for U.S. Appl. No. 09/835,752.
Office Action, mailed Oct. 21, 2002, for U.S. Appl. No. 09/835,752.
Reply to Office Action, mailed Jan. 29, 2008, for Application No. 10/870,342.
Notice of Allowance, mailed Nov. 9, 2007, for U.S. Appl. No. 10/870,342.
Reply to Office Action, mailed Sep. 24, 2007, for U.S. Appl. No. 10/870,342.
Office Action, mailed Mar. 23, 2007, for U.S. Appl. No. 10/870,342.
Office Action, mailed Feb. 27, 2006, for U.S. Appl. No. 10/870,342.
Office Action, mailed Mar. 16, 2010, for U.S. Appl. No. 11/794,635.
Reply to Office Action, mailed Jul. 14, 2010, for U.S. Appl. No. 11/794,635.
Notice of Allowance, mailed Jul. 26, 2010 for U.S. Appl. No. 11/749,635.

* cited by examiner

SEQUENCE LISTING

```
<160> NUMBER OF SEQ ID NOS: 25

<210> SEQ ID NO 1
<211> LENGTH: 128
<212> TYPE: PRT
<213> ORGANISM: Homo sapiens

<400> SEQUENCE: 1

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
        35                  40                  45

Asp Ala Cys Leu Ile Thr Lys Ala Gly Leu Gln Val Tyr Asn Lys Cys
    50                  55                  60

Trp Lys Phe Glu His Cys Asn Phe Asn Asp Val Thr Thr Arg Leu Arg
```

-continued

```
                65                  70                  75                  80
Glu Asn Glu Leu Thr Tyr Tyr Cys Cys Lys Lys Asp Leu Cys Asn Phe
                    85                  90                  95
Asn Glu Gln Leu Glu Asn Gly Gly Thr Ser Leu Ser Glu Lys Thr Val
                100                 105                 110
Leu Leu Leu Val Thr Pro Phe Leu Ala Ala Ala Trp Ser Leu His Pro
                115                 120                 125

<210> SEQ ID NO 2
<211> LENGTH: 103
<212> TYPE: PRT
<213> ORGANISM: Homo sapiens

<400> SEQUENCE: 2

Leu Gln Cys Tyr Asn Cys Pro Asn Pro Thr Ala Asp Cys Lys Thr Ala
1               5                   10                  15
Val Asn Cys Ser Ser Asp Phe Asp Ala Cys Leu Ile Thr Lys Ala Gly
                20                  25                  30
Leu Gln Val Tyr Asn Lys Cys Trp Lys Phe Glu His Cys Asn Phe Asn
                35                  40                  45
Asp Val Thr Thr Arg Leu Arg Glu Asn Glu Leu Thr Tyr Tyr Cys Cys
            50                  55                  60
Lys Lys Asp Leu Cys Asn Phe Asn Glu Gln Leu Glu Asn Gly Gly Thr
65                  70                  75                  80
Ser Leu Ser Glu Lys Thr Val Leu Leu Leu Val Thr Pro Phe Leu Ala
                    85                  90                  95
Ala Ala Trp Ser Leu His Pro
                100

<210> SEQ ID NO 3
<211> LENGTH: 103
<212> TYPE: PRT
<213> ORGANISM: Homo sapiens
<220> FEATURE:
<221> NAME/KEY: misc_feature
<222> LOCATION: (41)..(41)
<223> OTHER INFORMATION: Lys is glycated

<400> SEQUENCE: 3

Leu Gln Cys Tyr Asn Cys Pro Asn Pro Thr Ala Asp Cys Lys Thr Ala
1               5                   10                  15
Val Asn Cys Ser Ser Asp Phe Asp Ala Cys Leu Ile Thr Lys Ala Gly
                20                  25                  30
Leu Gln Val Tyr Asn Lys Cys Trp Lys Phe Glu His Cys Asn Phe Asn
                35                  40                  45
Asp Val Thr Thr Arg Leu Arg Glu Asn Glu Leu Thr Tyr Tyr Cys Cys
            50                  55                  60
Lys Lys Asp Leu Cys Asn Phe Asn Glu Gln Leu Glu Asn Gly Gly Thr
65                  70                  75                  80
Ser Leu Ser Glu Lys Thr Val Leu Leu Leu Val Thr Pro Phe Leu Ala
                    85                  90                  95
Ala Ala Trp Ser Leu His Pro
                100

<210> SEQ ID NO 4
<211> LENGTH: 103
<212> TYPE: PRT
<213> ORGANISM: Homo sapiens
<220> FEATURE:
<221> NAME/KEY: misc_feature
```

```
<222> LOCATION: (14)..(14)
<223> OTHER INFORMATION: Lys is glycated
<220> FEATURE:
<221> NAME/KEY: misc_feature
<222> LOCATION: (30)..(30)
<223> OTHER INFORMATION: Lys is glycated
<220> FEATURE:
<221> NAME/KEY: misc_feature
<222> LOCATION: (38)..(38)
<223> OTHER INFORMATION: Lys is glycated
<220> FEATURE:
<221> NAME/KEY: misc_feature
<222> LOCATION: (41)..(41)
<223> OTHER INFORMATION: Lys is glycated
<220> FEATURE:
<221> NAME/KEY: misc_feature
<222> LOCATION: (65)..(66)
<223> OTHER INFORMATION: Lys is glycated
<220> FEATURE:
<221> NAME/KEY: misc_feature
<222> LOCATION: (85)..(85)
<223> OTHER INFORMATION: Lys is glycated

<400> SEQUENCE: 4

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Val Thr Pro Phe Leu Ala
                85                  90                  95

Ala Ala Trp Ser Leu His Pro
            100

<210> SEQ ID NO 5
<211> LENGTH: 26
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: amino acid is deuterated-(d8)
<220> FEATURE:
<221> NAME/KEY: MISC_FEATURE
<222> LOCATION: (19)..(19)
<223> OTHER INFORMATION: amino acid is deuterated-(d8)

<400> SEQUENCE: 5

Thr Lys Ala Gly Leu Gln Val Tyr Asn Lys Cys Trp Lys Phe Glu His
1               5                   10                  15

Cys Asn Phe Asn Asp Val Thr Thr Arg Leu
            20                  25

<210> SEQ ID NO 6
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: amino acid is deuterated-(d8)

<400> SEQUENCE: 6
```

```
Ala Gly Leu Gln Val Tyr Asn Lys
1               5

<210> SEQ ID NO 7
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: amino acid is deuterated-(d8)

<400> SEQUENCE: 7

Phe Glu His Cys Asn Phe Asn Asp Val Thr Thr Arg
1               5                   10

<210> SEQ ID NO 8
<211> LENGTH: 8
<212> TYPE: PRT
<213> ORGANISM: Homo sapiens

<400> SEQUENCE: 8

Ala Gly Leu Gln Val Tyr Asn Lys
1               5

<210> SEQ ID NO 9
<211> LENGTH: 12
<212> TYPE: PRT
<213> ORGANISM: Homo sapiens

<400> SEQUENCE: 9

Phe Glu His Cys Asn Phe Asn Asp Val Thr Thr Arg
1               5                   10

<210> SEQ ID NO 10
<211> LENGTH: 15
<212> TYPE: PRT
<213> ORGANISM: Homo sapiens

<400> SEQUENCE: 10

Cys Trp Lys Phe Glu His Cys Asn Phe Asn Asp Val Thr Thr Arg
1               5                   10                  15

<210> SEQ ID NO 11
<211> LENGTH: 26
<212> TYPE: PRT
<213> ORGANISM: Homo sapiens

<400> SEQUENCE: 11

Thr Lys Ala Gly Leu Gln Val Tyr Asn Lys Cys Trp Lys Phe Glu His
1               5                   10                  15

Cys Asn Phe Asn Asp Val Thr Thr Arg Leu
            20                  25

<210> SEQ ID NO 12
<211> LENGTH: 5
<212> TYPE: PRT
<213> ORGANISM: Homo sapiens

<400> SEQUENCE: 12

Ala Gly Leu Gln Val
1               5

<210> SEQ ID NO 13
<211> LENGTH: 5
<212> TYPE: PRT
```

<213> ORGANISM: Homo sapiens

<400> SEQUENCE: 13

Gln Val Tyr Asn Lys
1               5

<210> SEQ ID NO 14
<211> LENGTH: 24
<212> TYPE: PRT
<213> ORGANISM: Homo sapiens

<400> SEQUENCE: 14

Ala Gly Leu Gln Val Tyr Asn Lys Cys Trp Lys Phe Glu His Cys Asn
1               5                   10                  15

Phe Asn Asp Val Thr Thr Arg Leu
            20

<210> SEQ ID NO 15
<211> LENGTH: 23
<212> TYPE: PRT
<213> ORGANISM: Homo sapiens

<400> SEQUENCE: 15

Ala Gly Leu Gln Val Tyr Asn Lys Cys Trp Lys Phe Glu His Cys Asn
1               5                   10                  15

Phe Asn Asp Val Thr Thr Arg
            20

<210> SEQ ID NO 16
<211> LENGTH: 24
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: amino acid is deuterated-(d8)
<220> FEATURE:
<221> NAME/KEY: MISC_FEATURE
<222> LOCATION: (17)..(17)
<223> OTHER INFORMATION: amino acid is deuterated-(d8)

<400> SEQUENCE: 16

Ala Gly Leu Gln Val Tyr Asn Lys Cys Trp Lys Phe Glu His Cys Asn
1               5                   10                  15

Phe Asn Asp Val Thr Thr Arg Leu
            20

<210> SEQ ID NO 17
<211> LENGTH: 23
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: amino acid is deuterated-(d8)
<220> FEATURE:
<221> NAME/KEY: MISC_FEATURE
<222> LOCATION: (17)..(17)
<223> OTHER INFORMATION: amino acid is deuterated-(d8)

<400> SEQUENCE: 17

Ala Gly Leu Gln Val Tyr Asn Lys Cys Trp Lys Phe Glu His Cys Asn
1               5                   10                  15

Phe Asn Asp Val Thr Thr Arg
            20

```
<210> SEQ ID NO 18
<211> LENGTH: 16
<212> TYPE: PRT
<213> ORGANISM: Homo sapiens

<400> SEQUENCE: 18

Cys Trp Lys Phe Glu His Cys Asn Phe Asn Asp Val Thr Thr Arg Leu
1               5                   10                  15

<210> SEQ ID NO 19
<211> LENGTH: 15
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: amino acid is deuterated-(d8)

<400> SEQUENCE: 19

Cys Trp Lys Phe Glu His Cys Asn Phe Asn Asp Val Thr Thr Arg
1               5                   10                  15

<210> SEQ ID NO 20
<211> LENGTH: 16
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: amino acid is deuterated-(d8)

<400> SEQUENCE: 20

Cys Trp Lys Phe Glu His Cys Asn Phe Asn Asp Val Thr Thr Arg Leu
1               5                   10                  15

<210> SEQ ID NO 21
<211> LENGTH: 23
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: amino acid is detectably labeled
<220> FEATURE:
<221> NAME/KEY: MISC_FEATURE
<222> LOCATION: (17)..(17)
<223> OTHER INFORMATION: amino acid is detectably labeled

<400> SEQUENCE: 21

Ala Gly Leu Gln Val Tyr Asn Lys Cys Trp Lys Phe Glu His Cys Asn
1               5                   10                  15

Phe Asn Asp Val Thr Thr Arg
            20

<210> SEQ ID NO 22
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: amino acid is detectably labeled

<400> SEQUENCE: 22

Ala Gly Leu Gln Val Tyr Asn Lys
1               5

<210> SEQ ID NO 23
<211> LENGTH: 15
```

```
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: amino acid is detectably labeled

<400> SEQUENCE: 23

Cys Trp Lys Phe Glu His Cys Asn Phe Asn Asp Val Thr Thr Arg
1               5                   10                  15

<210> SEQ ID NO 24
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: amino acid is detectably labeled

<400> SEQUENCE: 24

Phe Glu His Cys Asn Phe Asn Asp Val Thr Thr Arg
1               5                   10

<210> SEQ ID NO 25
<211> LENGTH: 25
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: amino acid is deuterated-(d8)
<220> FEATURE:
<221> NAME/KEY: MISC_FEATURE
<222> LOCATION: (19)..(19)
<223> OTHER INFORMATION: amino acid is deuterated-(d8)

<400> SEQUENCE: 25

Thr Lys Ala Gly Leu Gln Val Tyr Asn Lys Cys Trp Lys Phe Glu His
1               5                   10                  15

Cys Asn Phe Asn Asp Val Thr Thr Arg
            20                  25
```

MASS SPECTROMETRIC METHODS AND PRODUCTS

RELATED APPLICATIONS

The present application is a divisional of and claims priority under 35 U.S.C. §120 to U.S. patent application, U.S. Ser. No. 11/794,635, which is a national stage filing under U.S.C. §371 of international PCT application, PCT/US2006/000310, filed Jan. 6, 2006, which claims priority under 35 U.S.C. §119(e) from U.S. provisional patent application, U.S. Ser. No. 60/641,762, filed Jan. 6, 2005, each of which is incorporated herein by reference.

GOVERNMENT SUPPORT

This invention was made with Government support under grant number CA087427 from the National Institutes Health (NIH). The Government has certain rights in this invention.

FIELD OF THE INVENTION

The invention involves assays, diagnostics, kits, and assay components for mass spectrometry and other methods to determine levels of glycated CD59 in subjects.

BACKGROUND OF THE INVENTION

Diabetes Mellitus (diabetes) is a leading cause of morbidity and mortality in the adult population. This is primarily because diabetic patients tend to develop vascular complications that involve the kidneys (diabetic nephropathy), the retina (diabetic retinopathy), as well as large and small blood vessels in other organs (macro- and micro-vascular disease) including nerves (diabetic neuropathy). It is well established that the vascular complications of diabetes are caused by elevated blood glucose levels over long periods of time. Elevated blood glucose levels affect proteins by a process known as glycation. Different "glycated" proteins have been identified in diabetic subjects, including albumin, hemoglobin and others. Measurement of the extent of protein "glycation" of certain proteins is considered a valuable clinical tool to assess long term glycemic control and thereby the efficacy of diabetes treatment.

Glycation, the non-enzymatic attachment of glucose to proteins, is considered a major pathophysiological mechanism causing tissue damage in diabetic subjects. Glycation involves the reaction of glucose and/or other reducing sugars with amino groups in proteins resulting in the formation of a Schiff base or aldimine This labile adduct can tautomerize via the Amadori rearrangement to the more stable ketoamine. The function of the glycated protein may be impaired, depending on the location of the amino group(s) affected. For example, amino-terminal glycation of the β-chains of hemoglobin gives rise to the glycated hemoglobins (HbA1) in which responsiveness to 2,3-diphosphoglycerate is decreased and oxygen affinity increased. Glycation of the major thrombin inhibitor of the coagulation system, antithrombin III, decreases its affinity for heparin, and has been postulated to contribute to the hypercoagulable state associated with diabetes.

Mass spectrometry has been used for the examination of protein glycation in diabetes research. Low- and high-resolution mass spectra, GC/MS, collisional activation spectroscopy, ESI, and MALDI/MS have been used in research settings for structural identification and quantitative assessment of glycation end products and glycation of proteins. (Lapolla, A, et al., *Mass Spectrometry Reviews*, 2000, 19:279-304). These methods can be time-intensive and the markers for assessing glycation levels and related effects of increased glycation in diseases such as diabetes are not optimal or applicable for rapid, reliable clinical applications.

In the clinical assessment of diabetes, protein glycation in diabetic subjects is currently measured in blood by estimating the amount of glycated hemoglobin (hemoglobin A1c) through a complicated clinical test that requires extraction of a blood sample. Accordingly, there is a need for a simplified, faster, and less invasive method for rapid monitoring of protein glycation levels.

SUMMARY OF THE INVENTION

The inventor has discovered highly accurate and reproducible methods for quantitating CD59 and glycated CD59 in biological samples. The methods allow high-throughput, accurate analysis of samples, permitting a rapid and reliable measure for quantitating glycated protein in biological samples. The inventor has also discovered novel products and kits. The invention relates, in part, to the determination of the relative abundance of polypeptide products of the enzymatic digestion of glycated CD59, non-glycated CD59, and glycated and non-glycated CD59 fragments.

The presence of soluble CD59 in bodily fluids, such as urine (~5 µg/ml) and plasma (15-20 ng/ml), allow measurement of CD59 and glycated CD59 in the fluids, and the invention permits analysis of large number of samples through high-throughput mode. It is known that trypsin hydrolyzes peptide bonds on the N-terminus of positively charged amino acids such as K and R. Modification of amino acids, such as glycation of the amino acid side chain, can change the enzymatic digestion map of proteins. We have determined that glycated K41 on CD59 is no longer recognized as nonglycated CD59 and have developed novel methods that allow the determination of the level of glycated CD59 in biological samples. The novel methods are based in part on the altered digestion of glycated and non-glycated CD59. In one embodiment of the invention, the method of determining the level of glycated CD59 in a sample is a mass spectrometry method.

The glycation of the membrane protein known as CD59, a key regulator of the complement system, has been discovered to be involved in the pathogenesis of the vascular complications of diabetes. Glycated CD59 has now been identified in human urine, blood, saliva, and other biological fluids (see U.S. Pat. No. 6,835,545). The amount of glycated CD59 in human urine and other biological fluids correlates with glycemic control and levels of glycated hemoglobin. Detection of glycated CD59 in the urine and other biological fluids of diabetic patients can be used to monitor glycemic control in diabetic patients, and to select subjects for therapy.

According to one aspect of the invention, methods of determining the level of glycated CD59 in a sample are provided. The methods include digesting CD59 in a sample, identifying a peptide yielded by the digestion of the CD59 in the sample, and quantitating the identified peptide as a determination of the level of glycated CD59 in the sample. In some embodiments, the digestion is an enzymatic digestion. In some embodiments, the enzyme is trypsin. In some embodiments, the peptide is identified using immunoassay, gel electrophoresis, NMR, Western blotting, chromatography, or mass spectrometry. In some embodiments, the peptide is identified using mass spectrometry. In some embodiments, the peptide is quantitated by comparing the level of the peptide to the level of one or more additional peptides yielded by the digestion. In certain embodiments, the peptide is quantitated by comparing the level of the peptide to a control level. In some embodiments, the peptide identified is a peptide with one or more labels. In certain embodiments, the one or more labels is selected from the group consisting of stable isotopes, fluorescent labels, radiolabels, enzyme labels, and luminescent labels. In some embodiments, the peptide identified is a peptide having an amino acid sequence set forth as AGLQVYNK (SEQ ID NO:8), CWK, FEHCNFNDVTTR (SEQ ID NO:9), or CWKFEHCNFNDVTTR (SEQ ID NO:10). In some embodiments, the invention also includes spiking the sample with an internal standard before digestion. In some embodiments, the internal standard has one or more labels. In some embodiments, the one or more labels is selected from the group consisting of stable isotopes, fluorescent labels, radiolabels, enzyme labels, and luminescent labels. In some embodiments, the internal standard is a CD59 peptide. In some embodiments, the internal standard is a peptide comprising the amino acid sequence set forth as AGLQVYNKCWKFEHCNFNDVTTR (SEQ ID NO: 15). In some embodiments, the one or more labels are at one or more residues that correspond to A31 through K38 of mature CD59 peptide. In some embodiments, the one or more labels is on an amino acid of the portion of the sequence set forth as SEQ ID NO:15 that is AGLQVYNK (SEQ ID NO:8). In some embodiments, the one or more labels on AGLQVYNK (SEQ ID NO:8) are at one or more residues that correspond to residues A31, G32, L33, Q34, V35, Y36, N37, or K38 of mature CD59 peptide. In some embodiments, the label is at the residue of the peptide that corresponds to residue V35 of mature CD59 peptide. In some embodiments, the peptide has the amino acid sequence AGLQV$_{d8}$YNK (SEQ ID NO:6). In some embodiments, the one or more labels are at one or more residues that correspond to C39 through R53 of mature CD59 peptide. In certain embodiments, the one or more labels is on an amino acid of the portion of the sequence set forth as SEQ ID NO:15 that is CWKFEHCNFNDVTTR (SEQ ID NO:10). In some embodiments, the one or more labels are at one or more residues that correspond to residues C39, W40, K41, F42, E43, H44, C45, N46, F47, N48, D49, V50, T51, T52, or R53 of mature CD59 peptide. In some embodiments, the label is at the residue of the peptide that corresponds to residue F47 of mature CD59 peptide. In some embodiments, the peptide has the amino acid sequence CWKFEHCNF$_{d8}$NDVTTR (SEQ ID NO:19). In some embodiments, the peptide has the amino acid sequence CWKFEHCNF$_{d8}$NDVTTRL (SEQ ID NO:20). In some embodiments, the one or more labels is on an amino acid of the portion of the sequence set forth as SEQ ID NO:15 that is CWK. In some embodiments, the one or more labels is on an amino acid of the portion of the sequence set forth as SEQ ID NO:15 that is FEHCNFNDVTTR (SEQ ID NO:9). In some embodiments, the one or more labels are at one or more residues that correspond to F42 through R53 of mature CD59 peptide. In some embodiments, the one or more labels on FEHCNFNDVTTR (SEQ ID NO:9) are at one or more residues that correspond to residues F42, E43, H44, C45, N46, F47, N48, D49, V50, T51, T52, or R53 of mature CD59 peptide. In certain embodiments, the label is at the residue of the peptide that corresponds to residue F47 of mature CD59 peptide. In some embodiments, the peptide has the amino acid sequence FEHCNF$_{d8}$NDVTTR (SEQ ID NO:7). In some embodiments, one label is on an amino acid of the portion of SEQ ID NO:15 that is AGLQVYNK (SEQ ID NO:8), and one label is on an amino acid of the portion of SEQ ID NO:15 that is FEHCNFNDVTTR (SEQ ID NO:9). In certain embodiments, In some embodiments, the label on AGLQVYNK (SEQ ID NO:8) is at a residue that corresponds to residues A31, G32, L33, Q34, V35, Y36, N37, or K38 of mature CD59 peptide. In some embodiments, the label on FEHCNFNDVTTR (SEQ ID NO:9) is at a residue that correspond residues F42, E43, H44, C45, N46, F47, N48, D49, V50, T51, T52, or R53 of mature CD59 peptide. In some embodiments, the labels are at the residues of the peptide that correspond to residue V35 and F47 of mature CD59 peptide. In some embodiments, the labeled peptide is AGLQV$_{d8}$YNKCWKFEHCNF$_{d8}$NDVTTR (SEQ ID NO:17). In some embodiments, the labeled peptide is TKAGLQV$_{d8}$YNKCWKFEHCNF$_{d8}$NDVTTRL (SEQ ID NO:5). In some embodiments, the peptide is quantitated by comparing the level of the peptide determined in the spiked sample, the level of the internal standard added to the sample, and the level of one or more additional peptides yielded by the digestion. In some embodiments, the peptide is quantitated by comparing the level of the peptide to a control level. In some embodiments, the peptide quantitated is a peptide having the amino acid sequence set forth as AGLQVYNK (SEQ ID NO:8), CWK, FEHCNFNDVTTR (SEQ ID NO:9), or CWKFEHCNFNDVTTR (SEQ ID NO:10). In some embodiments, the peptide quantitated is labeled with one or more labels. In some embodiments, the one or more labels are selected from the group consisting of stable isotopes, fluorescent labels, radiolabels, enzyme labels, and luminescent labels. In some embodiments, the labeled peptide is AGLQVYNK (SEQ ID NO:8), or FEHCNFNDVTTR (SEQ ID NO:9). In some embodiments, the one or more labels are on one or more of the amino acids of the sequence set forth as AGLQVYNK (SEQ ID NO:8). In certain embodiments, the label on AGLQVYNK (SEQ ID NO:8) is at a residue that corresponds to residues A31, G32, L33, Q34, V35, Y36, N37, or K38 of mature CD59 peptide. In some embodiments, the labeled peptide is AGLQV$_{d8}$YNK (SEQ ID NO:6). In some embodiments, the one or more labels are on one or more of the amino acids of the sequence set forth as FEHCNFNDVTTR (SEQ ID NO:9). In some embodiments, the label on FEHCNFNDVTTR (SEQ ID NO:9) is at a residue that correspond to residues F42, E43, H44, C45, N46, F47, N48, D49, V50, T51, T52, or R53 of mature CD59 peptide. In some embodiments, the labeled peptide is FEHCNF$_{d8}$NDVTTR (SEQ ID NO:7). In some embodiments, the sample is a fluid sample. In some embodiments, the fluid sample is blood, urine, or saliva. In some embodiments, the sample is a tissue sample. In some embodiments, the sample is obtained from a subject. In some embodiments, the subject is diabetic. In some embodiments, the subject is at increased risk of becoming diabetic. In certain embodiments, the subject has received treatment for regulating blood sugar levels. In some embodiments, the subject has not received treatment for regulating blood sugar levels.

According to another aspect of the invention, methods of evaluating a treatment for regulating blood sugar levels are provided. The methods include obtaining a first level of glycated CD59 from a first sample obtained from a subject undergoing treatment for regulating blood sugar levels, obtaining a second level of glycated CD59 from a second sample obtained from the subject at least one day after obtaining the first level, comparing the first level to the second level as an indication of evaluation of the treatment, wherein the levels of glycated CD59 are determined by the methods set forth in any of the foregoing aspects and embodiments of the invention.

According to yet another aspect of the invention, methods of selecting a treatment for regulating blood sugar levels in a subject are provided. The methods include obtaining a level of glycated CD59 from a sample obtained from the subject, and selecting the treatment for regulating blood sugar levels in the subject based at least in part on the level obtained, wherein the level of glycated CD59 is determined by the methods set forth in any of the foregoing aspects and embodiments of the invention.

According to yet another aspect of the invention, methods for assessing onset, progression, or regression of a condition characterized by abnormal levels of glycated protein are provided. The methods include, obtaining a level of glycated CD59 from a sample obtained from a subject, and comparing the level to a control as an assessment of onset, progression, or regression of the condition, wherein the level of glycated CD59 is determined by the method set forth in any of the foregoing aspects and embodiments, of the invention.

According to another aspect of the invention, compositions are provided. The compositions include an isolated peptide comprising an amino acid sequence set forth as AGLQVYNKCWKFEHCNFNDVTTR (SEQ ID NO:15), wherein the sequence is labeled with one or more labels. In some embodiments, the isolated peptide has the amino acid sequence set forth as TKAGLQVYNKCWKFEHCNFNDVTTRL (SEQ ID NO:11). In some embodiments, the label is selected from the group consisting of stable isotopes, fluorescent labels, radiolabels, enzyme labels, and luminescent labels. In some embodiments, the one or more labels are at one or more peptide that correspond to residues A31, G32, L33, Q34, V35, Y36, N37, K38, C39, W40, K41, F42, E43, H44, C45, N46, F47, N48, D49, V50, T51, T52, or R53 of mature CD59 peptide. In some embodiments, the one or more labels is on one or more amino acids of the portion of the sequence set forth as SEQ ID NO:15 that is AGLQVYNK (SEQ ID NO:8). In some embodiments, the one or more labels is on one or more amino acids of the portion of the sequence set forth as SEQ ID NO:15 that is CWKFEHCNFNDVTTR (SEQ ID NO:10). In some embodiments, the one or more labels is on one or more amino acids of the portion of the sequence set forth as SEQ ID NO:15 that is CWK. In some embodiments, the one or more labels is on one or more amino acids of the portion of the sequence set forth as SEQ ID NO:15 that is FEHCNFNDVTTR (SEQ ID NO:9). In some embodiments, the label is at the residue that corresponds to residue V37 and/or F47 of mature CD59 peptide.

In some embodiments, the peptide has the amino acid sequence AGLQV$_{d8}$YNKCWKFEHCNF$_{d8}$NDVTTR (SEQ ID NO:17). In some embodiments, the peptide has the amino acid sequence AGLQV$_{d8}$YNKCWKFEHCNE$_{d8}$NDVTTRL (SEQ ID NO:16). In some embodiments, the labeled peptide is TKAGLQV$_{d8}$YNKCWKFEHCNE$_{d8}$NDVTTRL (SEQ ID NO:5).

According to yet another aspect of the invention, compositions are provided. The compositions include an isolated peptide having the amino acid sequence set forth as AGLQVYNK (SEQ ID NO:8). In some embodiments, the peptide is labeled with one or more labels. In some embodiments, the one or more labels are selected from the group consisting of stable isotopes, fluorescent labels, radiolabels, enzyme labels, and luminescent labels. In some embodiments, the one or more labels are at one or more residues that correspond to A31 through K38 of mature CD59 peptide. In some embodiments, the one or more labels on AGLQVYNK (SEQ ID NO:8) are at one or more residues that correspond to residues A31, G32, L33, Q34, V35, Y36, N37, or K38 of mature CD59 peptide. In some embodiments, the label is at the residue of the peptide that corresponds to residue V35 of mature CD59 peptide. In some embodiments, the peptide has the amino acid sequence AGLQV$_{d8}$YNK (SEQ ID NO:6).

According to yet another aspect of the invention, compositions are provided. The compositions include an isolated peptide having the amino acid sequence set forth as FEHCNFNDVTTR (SEQ ID NO:9). In some embodiments, the peptide has one or more labels. In some embodiments, the one or more labels are selected from the group consisting of stable isotopes, fluorescent labels, radiolabels, enzyme labels, and luminescent labels. In some embodiments, the one or more labels are at one or more residues that correspond to F42 through R53 of mature CD59 peptide. In some embodiments, the one or more labels on FEHCNFNDVTTR (SEQ ID NO:9) are at one or more residues that correspond to residues F42, E43, H44, C45, N46, F47, N48, D49, V50, T51, T52, or R53 of mature CD59 peptide. In some embodiments, the label is at the residue of the peptide that corresponds to residue F47 of mature CD59 peptide. In some embodiments, the peptide has the amino acid sequence FEHCNF$_{d8}$NDVTTR (SEQ ID NO:7).

According to another aspect of the invention, compositions are provided. The compositions include an isolated peptide comprising the amino acid sequence set forth as CWKFEHCNFNDVTTR (SEQ ID NO:10), wherein the peptide has one or more labels. In some embodiments, the peptide has the amino acid sequence set forth as CWKFEHCNFNDVTTRL (SEQ ID NO:18). In some embodiments, the one or more labels are selected from the group consisting of stable isotopes, fluorescent labels, radiolabels, enzyme labels, and luminescent labels. In some embodiments of any of the foregoing compositions, the one or more labels are at one or more residues that correspond to C39 through R53 of mature CD59 peptide. In some embodiments of any of the foregoing compositions, the one or more labels are at one or more residues that correspond to residues C39, W40, K41, F42, E43, H44, C45, N46, F47, N48, D49, V50, T51, T52, or R53 of mature CD59 peptide. In some embodiments, the label is at the residue of the peptide that corresponds to residue F47 of mature CD59 peptide. In some embodiments, the peptide has the amino acid sequence CWKFEHCNF$_{d8}$NDVTTR (SEQ ID NO:19). In some embodiments, the peptide has the amino acid sequence CWKFEHCNF$_{d8}$NDVTTRL (SEQ ID NO:20).

According to yet another aspect of the invention, compositions are provided. The compositions include an isolated peptide with the amino acid sequence set forth as CWK. In some embodiments, the isolated peptide has one or more labels. In some embodiments, the one or more labels are selected from the group consisting of stable isotopes, fluorescent labels, radiolabels, enzyme labels, and luminescent labels. In some embodiments, the one or more labels are at one or more residues that correspond to C39 through K41 of mature CD59 peptide. In some embodiments, the one or more labels are at one or more residues that correspond to C39, W40, K41 of mature CD59 peptide.

According to yet another aspect of the invention, kits for determining the level of glycated CD59 in a sample are provided. The kits include a package including a container containing an isolated peptide and instructions for the enzyme digest of a sample spiked with the isolated peptide to determine the presence and/or level of glycated CD59 in the sample. In some embodiments, the enzyme digest is a trypsin digest. In some embodiments, the isolated peptide is a CD59 peptide. In some embodiments, the CD59 peptide has one or more labels. In some embodiments, the one or more labels is selected from the group consisting of stable isotopes, fluorescent labels, radiolabels, enzyme labels, and luminescent labels. In some embodiments, the isolated peptide comprises the amino acid sequence set forth as CWKFEHCNFNDVTTR (SEQ ID NO:10) and has one or more labels. In some embodiments, the one or more labels are at one or more residues of CWKFEHCNFNDVTTR (SEQ ID NO:10) that correspond to residues C39, W40, K41, F42, E43, H44, C45, N46, F47, N48, D49, V50, T51, T52, or R53 of mature CD59 peptide. In some embodiments, the label is at the residue of CWKFEHCNFNDVTTR (SEQ ID NO:10) that corresponds to residue F47 of mature CD59 peptide. In some embodiments, the peptide has the amino acid sequence CWKFEHCNF$_{d8}$NDVTTR (SEQ ID NO:19). In some embodiments, the peptide has the amino acid sequence CWKFEHCNF$_{d8}$NDVTTRL (SEQ ID NO:20). In some embodiments, the isolated peptide has the amino acid sequence set forth as AGLQVYNKCWKFEHCNFNDVTTR (SEQ ID NO:15) and has one or more labels. In some embodiments, the isolated peptide has the amino acid sequence set forth as TKAGLQVYNKCWKFEHCNFNDVTTRL (SEQ ID NO:11) and has one or more labels. In some embodiments, the one or more labels are at one or more residues of that correspond to residues A31, G32, L33, Q34, V35, Y36, N37, K38, C39, W40, K41, F42, E43, H44, C45, N46, F47, N48, D49, V50, T51, T52, or R53 of mature CD59 peptide. In some embodiments, the label is at the residue that corresponds to residue V35 and/or F47 of mature CD59 peptide. In some embodiments, the peptide has the amino acid sequence AGLQV$_{d8}$YNKCWKFEHCNF$_{d8}$NDVTTR (SEQ ID NO:17). In some embodiments, the peptide has the amino acid sequence AGLQV$_{d8}$YNKCWKFEHCNE$_{d8}$NDVTTRL (SEQ ID NO:16). In some embodiments, the peptide has the amino acid sequence TKAGLQV$_{d8}$YNKCWKFEHCNF$_{d8}$NDVTTR (SEQ ID NO:25). In some embodiments, the peptide has the amino acid sequence TKAGLQV$_{d8}$YNKCWKFEHCNF$_{d8}$NDVTTRL (SEQ ID NO:5). In some embodiments, the label is at a residue of the peptide that corresponds to residue C39, W40, or K41 of mature CD59 peptide. In some embodiments, the kit also includes a container containing trypsin. In some embodiments, the peptide is lyophilized. In some embodiments, the peptide is packaged in an aqueous medium. In some embodiments, the kit also includes an antibody or antigen-binding fragment thereof that selectively binds a CD59 peptide.

According to yet another aspect of the invention, kits for determining the level of glycated CD59 in a sample are provided. The kits include a package that includes a container containing trypsin and a container containing an isolated CD59 peptide, and a container containing an antibody or antigen-binding fragment thereof that specifically binds to a trypsin-digest fragment of the CD59 peptide, and instructions for use of the antibody or antigen-binding fragment thereof to determine the presence and/or level of glycated CD59 in a sample. In some embodiments, the kit includes one or more CD59 peptides of any of the aforementioned embodiments or aspects of the invention.

These and other aspects of the invention will be described in greater detail below.

BRIEF DESCRIPTION OF THE SEQUENCES

Figure 1:
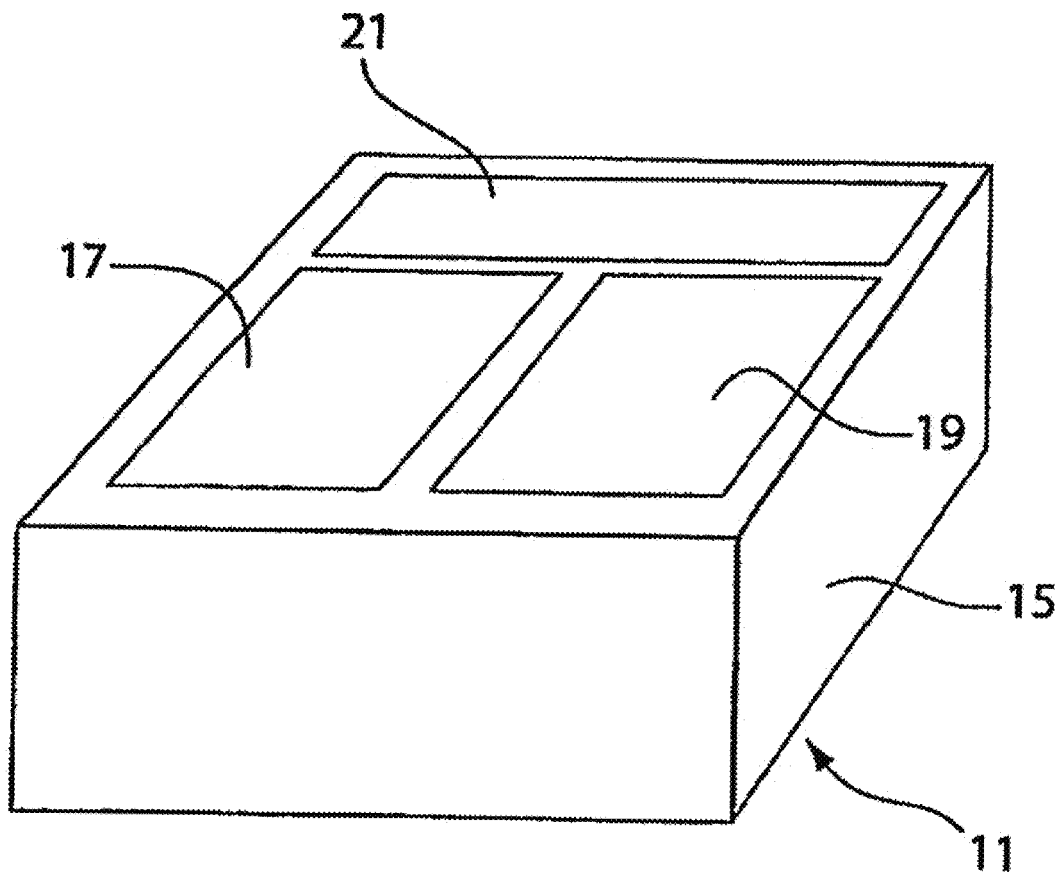
FIG. 1 is a schematic of a kit according to the invention.

SEQ ID NO:1 Amino acid sequence of full-length CD59 prior to removal of the signal peptide.
SEQ ID NO:2 Amino acid sequence of mature CD59 (signal peptide removed).
SEQ ID NO:3 Amino acid sequence of mature CD59 with glycated K41.
SEQ ID NO:4 Amino acid sequence of mature CD59 glycated at: K14, K30, K38, K41, K65, K66, and K85.
SEQ ID NO:5 TKAGLQVYNKCWKFEHCNFNDVTTRL with deuterated-$(d_8)$-$V_{(35)}$ and $d_8$-$F_{(47)}$.
SEQ ID NO:6 AGLQVYNK with deuterated-$(d_8)$-$V_{(35)}$.
SEQ ID NO:7 FEHCNFNDVTTR with deuterated-$d_8$-$F_{(47)}$.
SEQ ID NO:8 AGLQVYNK.
SEQ ID NO:9 FEHCNFNDVTTR.
SEQ ID NO:10 CWKFEHCNFNDVTTR.
SEQ ID NO:11 TKAGLQVYNKCWKFEHCNFNDVTTRL.
SEQ ID NO:12 AGLQV.
SEQ ID NO:13 QVYNK.
SEQ ID NO:14 AGLQVYNKCWKFEHCNFNDVTTRL.
SEQ ID NO:15 AGLQVYNKCWKFEHCNFNDVTTR.
SEQ ID NO:16 AGLQVYNKCWKFEHCNFNDVTTRL with deuterated $(d_8)$-$V_{(35)}$ and $d_8$-$F_{(47)}$.
SEQ ID NO:17 AGLQVYNKCWKFEHCNFNDVTTR with deuterated $(d_8)$-$V_{(35)}$ and $d_8$-$F_{(47)}$.
SEQ ID NO:18 CWKFEHCNFNDVTTRL.
SEQ ID NO:19 CWKFEHCNFNDVTTR with deuterated $d_8$-$F_{(47)}$.
SEQ ID NO:20 CWKFEHCNFNDVTTRL with deuterated $d_8$-$F_{(47)}$.
SEQ ID NO:21 AGLQVYNKCWKFEHCNFNDVTTR with a detectable label at $V_{(35)}$ and $F_{(47)}$.
SEQ ID NO:22 AGLQVYNK with a detectable label at $V_{(35)}$.
SEQ ID NO:23 CWKFEHCNFNDVTTR with a detectable label at $F_{(47)}$.
SEQ ID NO:24 FEHCNFNDVTTR with a detectable label at $F_{(47)}$.
SEQ ID NO:25 TKAGLQVYNKCWKFEHCNFNDVTTR with deuterated-$(d_8)$-$V_{(35)}$ and $d_8$-$F_{(47)}$.

DETAILED DESCRIPTION

The invention disclosed herein describes novel methods and compositions for detecting and measuring glycated CD59 levels in samples including biological samples. The methods of the invention for analysis of glycated CD59 in biological samples facilitate analysis of diseases in which the amount of CD59 glycation differs from normal levels. The level of glycation of CD59 is elevated in diabetes. The methods of the invention can be used to determine the onset, progression, and/or regression of diabetes or other diseases by using the methods to monitor levels of glycated CD59 in a subject. The invention, in part, relates to to the comparison of the relative abundance of polypeptide products of the enzymatic digestion of glycated CD59, non-glycated CD59, and glycated and non-glycated CD59 fragments as a determination of the level of glycated CD59 in a biological sample.

The inventor generated an antibody that recognizes the glycated form of human CD59 but not the non-glycated form nor other glycated proteins. Human CD59 was purified from human red blood cells and then glycated in vitro by exposure to glucose 0.5M for variable times. The specificity of the antibody then was documented by both Western blot analysis and ELISA. The antibody recognizes purified human CD59 after, but not before, glycation and does not recognize other glycated proteins such as glycated albumin, which is routinely used as a standard for glycated proteins.

The anti-glycated CD59 antibody was used to measure by ELISA the presence of glycated CD59 in human urine, plasma, kidney, nerve, and saliva. For each sample type, an ELISA using an antibody against total CD59 was also applied to the samples and the results expressed as the ratio of glycated-CD59/Total CD59 (i.e. the relative amount of glycated CD59 in each urine sample). The results indicated that glycated CD59 was found in human urine, plasma, kidney tissue, nerve tissue, and saliva and that the levels determined correlated well with the levels of glycated hemoglobin (HbA1C) in blood, the current clinical standard for assessment of glycemic exposure in diabetic patients.

In addition, in contrast to markers of glycation such as hemoglobin, glycation of CD59 is believed to be involved in the pathogenesis of the vascular complications of diabetes. Accordingly, clinical evaluation of glycated CD59 in urine or other body fluid is a direct measure for vascular damage induced by glycation. Without wishing to be bound by any particular theory, it is believed that patients with abnormally high levels of glycated CD59 (e.g. K41-glycated CD59) in urine or other body fluid will either have or will be more prone to develop vascular complications of diabetes.

The inventor has now discovered novel methods, including mass spectrometry methods, which can be used to assess the level of glycated CD59 these samples from a subject. The methods, products, and kits of the invention are based, in part, on the novel discovery that the relative abundance of polypeptide products of enzymatic digestion of glycated CD59, non-glycated CD59, and glycated and non-glycated CD59 fragments can be compared and can provide a determination of the level of glycated CD59 in a biological sample.

As used herein, CD59 (also known as membrane inhibitor of reactive lysis [MIRL], protectin, HRF20 and H19) and glycated CD59 are polypeptides having the amino acid sequence identity of Accession No. M95708 (Davies, A., et al., *Journal J. Exp. Med.* 170 (3), 637-654 (1989)). A nucleic acid sequence encoding CD59 also is provided by Davis, A, et al. A CD59 sequence is provided herein as SEQ ID NO:1, which represents non-glycated CD59. The sequence of non-glycated CD59 that is present in mature form in cells and tissues is set forth as SEQ ID NO:2. The sequence of mature CD59 that is glycated at K41 is set forth as SEQ ID NO:3. The sequence of mature CD59 that is glycated at K14, K30, K38, K41, K65, K66, and K85 is set forth as SEQ ID NO:4.

As used herein, "glycated CD59" means CD59 that has been glycated. In some embodiments, glycated CD59 is CD59 that has been glycated at the amino acid residue that corresponds to the amino acid residue number 41 of full-length mature CD59, which is set forth herein as SEQ ID NO:2. The residue in position 41 of full-length mature CD59 is a lysine, and this lysine in the full length and the residue that corresponds to this position in fragments is referred to herein as "K41". CD59 in which the K41 residue is glycated is referred to herein as K41-glycated CD59. In some embodiments, a glycated lysine residue is a glycocytol-lysine residue. Thus, a glycated CD59 or fragment thereof may be glycated by the inclusion of a glycocytol-lysine residue. In certain embodiments, a lysine residue of CD59 or a fragment thereof may be glycated by contacting the CD59 or fragment thereof with glycating sugars (e.g. glucose, ribose, or glycose-6-phosphate).

It is known that the CD59 polypeptide sequence includes a 25 amino acid signal peptide that is cleaved when CD59 is produced, thus forming the mature CD59 protein sequence. As would be understood by one of ordinary skill in the art, CD59 in a sample obtained from a subject would be CD59 from which the signal peptide has been cleaved. The sequence of the CD59 polypeptide prior to removal of the signal peptide is provided herein as SEQ ID NO:1 and the amino acid sequence of mature CD59 polypeptide is set forth herein as SEQ ID NO:2. As used herein, the terms "peptide" and "polypeptide" are used interchangeably.

Glycation of CD59, including, but not limited to K41 glycation of CD59, is correlated to abnormal blood sugar levels, and glycation of CD59 interferes with the normal activity of CD59. CD59 functions normally by binding to the terminal components of the membrane attack complex of complement (MAC), thereby interfering with membrane insertion and polymerization of the C9 component of complement. Glycation at the K41 of CD59 interferes with CD59's ability to prevent the assembly of the MAC. While not wishing to be bound by any theory it is believed that, as a result of glycation of CD59, the MAC is permitted to be activated and leads to the development of proliferative chronic diabetic complications. Indeed, the present inventor has shown that the membrane attack complex stimulates proliferation of fibroblasts, smooth muscle, mesangial and other cells, in part by releasing growth factors such as FGF and PDGF from MAC-targeted endothelium. The MAC also induces increased synthesis of extracellular matrix proteins by mesangial cells. Thus, increased MAC deposition in diabetic tissues is believed to induce growth factor release from endothelium, which stimulates cell proliferation in the vascular wall and contributes to the expansion of the extracellular matrix and to the glomerulosclerosis that characterizes diabetic nephropathy.

The invention also involves fragments of the foregoing proteins. A fragment of CD59 comprises at least 3, 4, 5, 6, 7, 8, 9, 10, 11, 12, 13, 14, 15, 16, 17, 18, 19, or 20 or more contiguous amino acids of CD59 having a consecutive sequence found in CD59 or a modified CD59 sequence as described herein. As used herein, the term "CD59 peptide" includes full-length CD59 and peptides that have an amino acid sequence that corresponds to a portion or fragment of full-length CD59. As used herein, the term "portion" means part of the whole. In some embodiments, a fragment includes K41, which may or may not be glycated K41. Polypeptide fragments of the invention also include fragments of CD59 generated by enzymatic digestion of CD59. In some embodiments, the enzymatic digestion is trypsin digestion. Fragments of CD59 molecules include fragments of labeled $CD59_{(29-54)}$ peptide, including deuterated-$(d_8)$-$V_{(35)}$ and $d_8$-$F_{(47)}$ $CD59_{(29-54)}$ peptide TKAGLQVYNKCWKFEHCNFNDVTTRL (SEQ ID NO:5), such as the fragments AGLQV$_{d8}$YNK (SEQ ID NO:6), CWK, and FEHCNF$_{d8}$NDVTTR (SEQ ID NO:7). The non-deuterated $CD59_{(29-54)}$ peptide (TKAGLQVYNKCWKFEHCNFNDVTTRL (SEQ ID NO:11) and enzymatic cleavage fragments thereof are also peptides of the invention.

As used herein, the term "native peptide" means a peptide that is unlabeled and the term "labeled peptide" means a peptide that includes a label. Thus, any native polypeptide of the invention may be referred to as a labeled polypeptide if it includes the same amino acid sequence as the native polypeptide and also includes one or more labels. As will be understood by those of ordinary skill in the art, the nomenclature used herein for the fragments of CD59 peptide and positions of labels on CD59 peptide and fragments thereof, correspond to the residue numbers in the mature CD59 molecule. For example, the residues indicated as 29-54 in the name of the $CD59_{(29-54)}$ peptide correspond to residues 29-54 in the mature CD59 peptide and detectable labels at $V_{(35)}$ and $F_{(47)}$ are on the residues that correspond to $V_{35}$ and $F_{47}$ of mature CD59 peptide.

Additional fragments of the invention include enzyme digestion products of glycated and non-glycated CD59. In some embodiments, the enzyme digestion is a trypsin digestion. Fragments that result from trypsin digestion of non-glycated CD59 include at least AGLQVYNK (SEQ ID NO:8), CWK, and FEHCNFNDVTTR (SEQ ID NO:9). Fragments that result from the trypsin digestion of glycated CD59 include at least AGLQVYNK (SEQ ID NO:8) and CWKFEHCNFNDVTTR (SEQ ID NO:10). The digestion products that result from trypsin digestion of glycated CD59 differ from the digestion products that result from trypsin digestion of non-glycated CD59, thus permitting the comparison of the resulting digestion products as a relative measure of the amounts of glycated and non-glycated CD59 in a digested sample.

In some embodiments, a CD59 polypeptide of the invention includes a detectable label. In some embodiments, the detectable label is selected from the group consisting of a fluorescent label, an enzyme label (e.g. biotinylation, etc.), a radioactive label (e.g $^{14}C$, $^{3}H$, etc.), a nuclear magnetic resonance active label, a luminescent label (e.g fluorescein isothiocyanate, etc.), and a chromophore label. In some embodiments, the label is a label used for mass spectrometry methods. In some embodiments, stable isotopes may be used as labels, including, but not limited to: carbon 13 ($^{13}C$), protium ($^{1}H$), deuterium ($^{2}H$), nitrogen 15 ($^{15}N$), oxygen 17 ($^{17}O$), oxygen 18 ($^{18}O$), sulfur 34 ($^{34}S$), sulfur 33 ($^{33}S$), chlorine 37 (37Cl), bromine 81 ($^{81}Br$), and beryllium 10 ($^{10}Be$). In some embodiments, a CD59 polypeptide of the invention is a deuterated polypeptide. Additional labels suitable for mass spectrometry and other detection methods useful in the methods and kits of the invention will be known to those of skill in the art. In the methods and kits of the invention, a label may be attached to a peptide, e.g. covalently attached, and/or may be integrated into the peptide. As used herein the term "integrated into" means that the label may be a part of the peptide—e.g. a peptide may be synthesized with a deuterated amino acid, thus the label is included in the polypeptide and is a part of the polypeptide.

According to one aspect of the invention, the detectable label may be attached to or integrated into a CD59 polypeptide or fragments thereof, such that upon enzymatic digestion, the label remains attached to or as an integral part of a digestion product of the CD59 polypeptide or CD59 polypeptide fragments. For example, TKAGLQVYNKCWKFEHCNFNDVTTRL (SEQ ID NO:11) may be labeled with one or more detectable labels such that following trypsin digestion, the detectable label remains on one or more of the fragments generated in the digest. For example, a label may be attached to SEQ ID NO:11 such that following digestion with trypsin, the label will remain on a digestion product of the CD59 polypeptide fragment. Thus, if SEQ ID NO:11 was originally labeled with a detectable label on $V_{(35)}$, after trypsin digestion of a sample containing the labeled SEQ ID NO:11, the label will be on the digestion product: FEHCNFNDVTTR (SEQ ID NO:9).

In some embodiments of the invention, a sample is spiked with a labeled CD59 polypeptide or spiked with labeled CD59 polypeptide fragments. When added to a sample, the detectably labeled CD59 or CD59 fragments serve as an internal standard in the sample. As used herein, the term "to spike" means to add the internal standard to a sample. The spiking of a sample with a known amount of a CD59 polypeptide or fragment thereof allows detection and quantitation of the digestion products of the spike CD59 polypeptide (e.g. the detectibly labeled CD59 polypeptide) and the determination of the relative amounts of other digestion products in the sample. As used herein, the term "internal standard" means a known amount of a CD59 polypeptide or fragment thereof. In some embodiments, the internal standard is a detectably labeled CD59 polypeptide or detectably labeled fragment thereof. The presence of a detectable label on a fragment of a digested sample allows the quantities of labeled and unlabeled fragments to be determined and compared allowing the quantitation of the amount of glycated and/or non-glycated CD59 in the sample.

As provided herein, $CD59_{(29-54)}$ peptide TKAGLQVYNKCWKFEHCNFNDVTTRL (SEQ ID NO:5) with deuterated-$(d_8)$-$V_{(35)}$ and $d_8$-$F_{(47)}$ is an example of a labeled CD59 fragment that can be added as an internal standard to a sample in some embodiments of the invention. It will be understood by those of ordinary skill in the art that in some embodiments of the invention the label on the CD59 polypeptide may be in a different position on the polypeptide (e.g. on a residue other than $V_{(35)}$ or $F_{(47)}$). In addition, the label may be a label other than a deuterated label. Thus, for use with mass spectrometry detection methods and related kits of the invention, a deuterated label or other mass spectrometry-appropriate label may be used. One of ordinary skill will understand that for use with other detection methods such as chromatography, ELISA, or electrophoresis, other (e.g. method-appropriate) detectable labels may be used.

Additional CD59 polypeptide fragments are useful in the methods and kits of the invention. For example a deuterated or non-deuterated polypeptide that includes fewer or more amino acids than TKAGLQVYNKCWKFEHCNFNDVTTRL (SEQ ID NO:11) can be used in the methods of the invention. For example, deuterated or non-deuterated polypeptides with an amino acid sequence AGLQVYNKCWKFEHCNFNDVTTRL (SEQ ID NO:14) or AGLQVYNKCWKFEHCNFNDVTTR (SEQ ID NO:15) can be used in the methods of the invention, as can a polypeptide that is 1, 2, 3, 4, 5, 6, 7, 8, or more amino acid residues shorter than the sequence set forth as SEQ ID NO:11, as long as the fragment permits quantitation of glycated CD59 using a method provided herein.

In one embodiment, the fragment is AGLQVYNKCWKFEHCNFNDVTTR (SEQ ID NO:15). This fragment, if glycated at K41, will be digested by trypsin into AGLQVYNK (SEQ ID NO:8) and CWKFEHCNFNDVTTR (SEQ ID NO:10) but if non-glycated the fragment will be digested into: AGLQVYNK (SEQ ID NO:8), CWK, and FEHCNFNDVTTR (SEQ ID NO:9). In some embodiments of the invention, the sequence: AGLQVYNKCWKFEHCNFNDVTTR (SEQ ID NO:15) includes one or more labels such that when the fragment is digested by trypsin, a label will be on fragments generated by the digestion. For example, AGLQVYNKCWKFEHCNFNDVTTR (SEQ ID NO:15) may include a label at $V_{(35)}$ and $F_{(47)}$ residues as in AGL QV$_{label}$YNKCWKFEHCNF$_{label}$NDVTTR (SEQ ID NO:21). In some embodiments the label is a deuterated label. After digestion of the glycated labeled polypeptide set forth as SEQ ID NO:15, the resulting fragments will be AGLQV$_{label}$YNK (SEQ ID NO:22) and CWKFEHCNF$_{label}$NDVTTR (SEQ ID NO:23). If the labeled polypeptide set forth as SEQ ID NO:15 is non-glycated the resulting digest fragments will be AGLQV$_{label}$YNK (SEQ ID NO:22), CWK, and FEHC NF$_{label}$NDVTTR (SEQ ID NO:24). The production of different digestion products, and in some embodiments, differentially labeled digestion products allows identification of the fragments generated by trypsin digestion and identification of the presence of glycated and non-glycated CD59 in the digested sample. One of ordinary skill will understand that the residue on which a label is attached can vary from the example provided above. The specific residue that is labeled is selected based on it enabling one to differentiate the digestion products from glycated versus non-glycated CD59.

In some embodiments, a fragment of CD59 that is useful in the methods of determining the amount of glycated CD59 in a sample can be a fragment of CD59 larger than the fragment set forth as SEQ ID NO:11. In some embodiments of the invention, the spike polypeptide can be full-length non-glycated CD59 or can be non-glycated CD59 that is one or more amino acid shorter than full-length CD59. In some embodiments, the fragment of CD59 can be labeled (e.g. deuterated in the manner of SEQ ID NO:5 or otherwise labeled). The fragments can be used to determine the amount of glycated CD59 in a sample with a mass spectrometry method or other determining method provided herein.

According to some aspects of the invention, isolated CD59 polypeptides are provided. By "isolated", it is meant present in sufficient quantity to permit its identification or use according to the procedures described herein. Isolated includes (1) synthesized, (2) selectively produced by expression cloning or (3) purified as by mass spectrometry, immunoprecipitation, chromatography, or electrophoresis. Because an isolated material may be admixed with a carrier in a preparation, such as, for example, for adding to a sample or for analysis, the isolated material may comprise only a small percentage by weight of the preparation.

The term "isolated polypeptide" may also mean a polypeptide that is not in association with amino acids with which it is naturally found. For example, an isolated AGLQVYNK (SEQ ID NO:8) polypeptide is a polypeptide that does not include the amino acids that correspond to the amino acids adjacent to this portion of full-length, mature CD59 polypeptide. Thus, for isolated SEQ ID NO:8, the amino acids beginning at (and extending outward from) the amino acids K and C that are adjacent to the SEQ ID NO:8 portion of the sequence in full-length, mature CD59, are not present in isolated SEQ ID NO:8. Thus, the term "isolated" means the polypeptide is separated from (free of) the adjacent amino acids that would be present in mature, full-length CD59 polypeptide.

According to one aspect of the invention, isolated glycated CD59 polypeptides and fragments are provided. An isolated glycated CD59 polypeptide or fragment thereof may include CD59 polypeptide or fragment thereof (1) selectively produced by expression cloning and glycation or (2) purified as by mass spectrometry, immunoprecipitation, chromatography, or electrophoresis. Because an isolated material may be admixed with a carrier or solvent in a preparation, the isolated material may comprise only a small percentage by weight of the preparation. The material is none-the-less isolated in that it has been separated from the substances with which it typically is associated. According to the present invention, the isolated glycated CD59 represents at least 10%, 20%, 30%, 40%, 50%, 60%, 70%, 80%, 90% or 95% of the CD59 in the composition (i.e. percentage of total CD59 both glycated and nonglycated CD59).

According to another aspect of the invention, pure glycated CD59 is provided. In some embodiments, the pure glycated CD59 is K41-glycated CD59. Isolated proteins or polypeptides may, but need not be, pure. The term "pure" means the proteins or polypeptides are essentially free of other substances with which they may be found in nature or in in vivo systems to an extent practical and appropriate for their intended use. Pure polypeptides may be produced by techniques well-known in the art. As used herein, "pure" glycated CD59 means at least 95% of the total CD59 is glycated CD59.

As used herein, the term "glycated CD59" polypeptide includes mature CD59 polypeptide with one or more glycated lysine (K) residues. In some embodiments, the glycated lysine residue of CD59 is residue K41 of mature CD59. One of ordinary skill in the art will understand that a fragment of CD59 can be compared to mature full-length CD59, and the presence of a residue in that fragment is said to "correspond" to the residue of mature CD59. As used herein therefore, residue positions for lysines are identified as they occur in mature CD59, whether that residue is part of mature CD59 or part of a fragment or modified fragment. Thus, K41 maintains that designation in mature CD59 or fragments thereof. In some embodiments, the glycated lysine residue in a fragment of CD59 is K41. In certain embodiments of the invention, the glycated residue of CD59 or a fragment thereof is or corresponds to K14, K30, K38, K65, K66, or K85 of mature CD59 polypeptide. In some embodiments, more than one K residue is glycated.

The methods of the invention include mass spectrometry analysis. Mass spectrometry is an analytical method that is used for used for quantitative and qualitative analysis of the samples and materials (e.g., biological samples). In general, a mass spectrometry system uses an ion source to produce electrically charged particles (e.g., molecular or polyatomic ions) from the material to be analyzed. The electrically charged particles are introduced to the mass spectrometer and separated by a mass analyzer based on the particles' respective mass-to-charge ratios. The abundance of the separated electrically charged particles are detected and a mass spectrum of the material is produced. The mass spectrum provides information about the mass-to-charge ratio of a particular compound in a mixture sample and, in some cases, molecular structure of that component in the mixture. In some embodiments of the invention, mass spectrometry is isotope ratio mass spectrometry.

Mass spectrometers convert components of a sample into rapidly moving gaseous ions and separate them on the basis of their mass-to-charge ratios. Generally, mass spectrometers include an ionization means and a mass analyzer. A number of different types of mass analyzers are known in the art. These include, but are not limited to, magnetic sector analyzers, electrostatic analyzers, quadrapoles, ion traps, time-of-flight mass analyzers, and fourier transform analyzers. In addition, two or more mass analyzers may be coupled (MS/MS) first to separate precursor ions, then to separate and measure gas phase fragment ions.

Mass spectrometers may also include one of a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization. In addition, mass spectrometers may be coupled to separation means such as gas chromatography (GC) and high performance liquid chromatography (HPLC).

In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer. Thus, in GC/MS analysis, a mixture of compounds to be analyzed is first injected into the gas chromatograph and is vaporized in a heated chamber. The gas mixture then goes through a GC column, where the compounds are separated as they interact with the column A gas chromatogram for the sample is generated showing peaks of the separated compounds from sample, and the separated compounds immediately enter the mass spectrometer for MS analysis.

There are three general elements or components that make up a mass spectrometry system including: the ionizer, the ion analyzer, and the detector. One of ordinary skill in the art will understand how to apply the MS methods and embodiments of the invention utilizing MS systems that include combinations of the MS components and elements described herein, as well as other art-known MS methods and procedures.

Samples must be in gaseous form for MS analysis. Thus, in some embodiments, a sample may be vaporized by heating. After it is vaporized the sample passes through the electron ionization component of the MS system. One of ordinary skill will recognize that a number of ionization methods are known in the art that can be used in the methods of the invention. For example, electron ionization is useful in conjunction with GS/MS. Other methods of ionization that are useful in the methods of the invention include, but are not limited to: Electrospray Ionization (ESI), Matrix-Assisted Laser Desorption/Ionization Mass Spectrometry (MALDI-MS), atmospheric pressure chemical ionization (APCI), Fast Atom Bombardment (FAB), chemical ionization (CI) and Inductively Coupled Plasma (ICP) ionization.

After ionization, the next stage of MS is mass analysis. This occurs in the mass analyzer of the MS. The mass analyzer separates ions within a selected range of mass-to-charge (m/z) ratios. The basis for this separation generally is through the use of magnetic fields, electric fields, or measurement of time it takes for an ion to travel a specified distance. Known methods for mass analysis in MS methods include, but are not limited to: double focusing magnetic sector mass analysis, tandem mass spectrometry, Quadrupole mass analysis, Quadrupole ion trap mass analysis, Fourier-Transform Mass Spectrometry (FTMS), and Time-of-Flight (TOF). The final element of MS analysis is ion detection. Ion detection means known in the art include, but are not limited to: faraday cup detectors, electron multiplier detectors, and photomultiplier conversion dynode detectors.

One of ordinary skill in the art will understand how methods and kits of the invention may be optimized using combinations of the MS components, elements, and method described herein as well as other art-known MS apparatus and apparatus.

In one embodiment of the invention, the typsin digestion products of a sample may be measured directly by mass spectrometry. In another embodiment, typsin digestion products of a sample may be partially purified, or optionally isolated, prior to mass spectral analysis. A biological sample, e.g. a sample from a subject, may be prepared for mass spectrometry analysis using standard procedures known in the art. An example of sample preparation methods useful in the methods of the invention is provided in the Example section.

For mass spectrometry analysis of the invention, an internal standard of a known amount of a CD59 peptide is added to the sample prior to trypsinization. In some embodiments, the internal standard is the $CD59_{(29-54)}$ peptide TKAGLQV$_{d8}$YNKCWKFEHCNF$_{d8}$NDVTTRL (SEQ ID NO:5), which includes deuterated-($d_8$)-V$_{(35)}$ and $d_8$-F$_{(47)}$, is added to each sample prior to trypsinization. As used herein, the term "spike" means to add the internal standard to a sample. For example, a spiked sample is a sample to which an internal standard of $CD59_{(29-54)}$ peptide TKAGLQV$_{d8}$YNKCWKFEHCNF$_{d8}$NDVTTRL (SEQ ID NO:5) has been added. In important embodiments, the amount of the internal standard added is a known amount. The sample with the internal standard added (spiked sample) is then the sample is trypsinized to digest the spiked sample. Trypsin digestion can be done under conditions that allow the digestion of the spiked sample to generate fragments of the polypeptides in the sample. For example, the enzymatic digestion is carried out under conditions that allow the glycated and non-glycated CD59 and the internal standard $CD59_{(29-54)}$ peptide TKAGLQV$_{d8}$YNKCWKFEHCNF$_{d8}$NDVTTRL; SEQ ID NO:5) to be digested into detectable fragments. In some embodiments, the digestion may be digestion of the full-length starting polypeptide to completion. In the embodiments of the invention, the conditions for the enzymatic digestion of the spiked sample are sufficient for the glycated, non-glycated, and $CD59_{(29-54)}$ peptide to be digested into the fragments described herein. Digestion conditions may include a temperature of up to about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., or more and a length of digestion from up to about 15, 16, 17, 18, 19, 20, 21, 22, 23, 24, 25, 26, 27, 28, 29, 30, 31, 32, 33, 34, 35, 36, 37, 38, 39, 40, or more minutes. The pH of the digest reaction may be in a range appropriate for the enzyme, e.g. trypsin. For example, for a trypsin digestion, the pH may optimally range from about 7 to about 9 including any pH level in between 7 and 9. In one embodiment, the temperature of the digestion is about 37° C. and the length of time of the digestion is about 30 minutes.

One of ordinary skill in the art will recognize that the optimal temperature, pH, and length of time of the trypsin digestion can be varied based on factors such as enzyme activity, enzyme amount, etc. In addition, the length of time of the digestion may also be varied depending on the temperature of the digestion and vice versa. One of skill in the art can easily optimize the time, temperature, concentration, etc. of the trypsin digestion conditions for use in the methods and kits of the invention. One example of conditions that can be used in the methods of the invention, although not intended to be limiting, is a 30 minute digestion at 37° C.

In some embodiments of the invention, the enzyme used in the digestion methods to determine the level of glycated CD59 is trypsin. Trypsin may be naturally obtained trypsin, or may be artificial trypsin, e.g. recombinant trypsin. The source of trypsin useful in the methods of the invention, include, but is not limited to, bovine, porcine, human, fish, etc. The trypsin of may be free or immobilized trypsin. The trypsin may be treated with an agent to remove chymotrypsin activity. For example the trypsin may be treated with diphenyl carbamyl chloride (DPCC) or with L-(tosylamido-2-phenyl) ethyl chloromethyl ketone (TPCK) to reduce the activity level of chymotrypsin. Those of ordinary skill will understand that trypsin is known by other names and can be obtained in various levels of purity, grade, and forms. For example the trypsin may be highly purified for use in mass spec. The trypsin may be modified trypsin. An example of a modified trypsin, though not intended to be limiting is trypsin modified by reductive methylation to increase stability.

Trypsinization of the urine or plasma sample (or other biological sample or control) with the added internal standard $d_8$-$CD59_{(29-54)}$ peptide yields the different polypeptide digestion products of CD59 depending on whether the CD59 is glycated or non-glycated CD59. If the CD59 is non-glycated CD59, the tryptic digestion methods of the invention yields the following peptides: AGLQVYNK (SEQ ID NO:8), CWK, and FEHCNFNDVTTR (SEQ ID NO:9). Trypsin digestion of $CD59_{(29-54)}$ peptide TKAGLQV$_{d8}$YNKCWKFEHCNF$_{d8}$NDVTTRL (SEQ ID NO:5) yields AGLQV$_{d8}$YNK (SEQ ID NO:6), CWK, and FEHCNF$_{d8}$NDVTTR (SEQ ID NO:7). In contrast: trypsin digestion of glycated CD59 yielded only two peptides because glycated CD59 is not cleaved at the glycated K41 site: AGLQVYNK (SEQ ID NO:8) and CWKFEHCNFNDVTTR (SEQ ID NO:10).

Isotopically labeled and natural peptides ionize in an identical manner, thus the ionization of the internal standard peptides [AGLQV$_{d8}$YNK (SEQ ID NO:6) and FEHCNF$_{d8}$NDVTTR (SEQ ID NO:7)] is the same as the ionization of the peptides derived from the subject's CD59 [AGLQVYNK (SEQ ID NO:8) and FEHCNFNDVTTR (SEQ ID NO:9)]. Thus, peptides derived from either the internal standard or the subject's CD59 have identical charge but a different mass of eight (8) units that allows their unambiguous identification and quantitation provided that the amount of the labeled CD59$_{(29-54)}$ peptide added to the sample was known. The mass difference of 8 is the result of the presence of V$_{d8}$ in AGLQV$_{d8}$YNK (SEQ ID NO:6) and of F$_{d8}$ in FEHCNF$_{d8}$NDVTTR (SEQ IDNO:7).

The AGLQVYNK (SEQ ID NO:8) peptide is generated by the trypsin digestion of both glycated and non-glycated CD59. Thus, the quantitative estimate of AGLQVYNK (SEQ ID NO:8) represents total CD59 in the sample. In contrast, the FEHCNFNDVTTR (SEQ ID NO:9) peptide is only generated by the trypsin digestion of non-glycated CD59. Thus, the quantitative estimate of FEHCNFNDVTTR (SEQ ID NO:9) represents non-glycated CD59 in the sample. The difference between the amount of total CD59 and the amount of non-glycated CD59 is the amount of glycated CD59 in the sample. In some embodiments of the invention, a sample is a control sample, e.g. a sample from a subject known to not have a diabetic disorder or abnormal ability to metabolize glucose.

As detailed herein, the mass spectrometric methods of the invention may be used for example to identify and quantitate CD59 protein (including K41-nonglycated CD59) and/or glycated CD59 protein including K41-glycated protein. Thus, in the method and products of the invention, the inclusion of a known amount of an internal standard (e.g. CD59$_{(29-54)}$ peptide TKAGLQV$_{d8}$YNKCWKFEHCNF$_{d8}$NDVTTRL (SEQ ID NO:5) in the sample to be tested permits the determination of the level of glycated CD59 in the sample.

In other embodiments of the invention, the fragments of CD59 and glycated CD59 generated with enzymatic digestion, e.g. trypsin digestion, are determined using non-mass spectrometric methods. For example additional methods such as immunoassay, (e.g. ELISA, etc.) gel electrophoresis, Western blot analysis, NMR, chromatography, etc. may be used to identify the fragments produced by the digestion of glycated and non-glycated CD59. For example, as described above, if non-glycated CD59 is digested by typsin the resultant peptides are: AGLQVYNK (SEQ ID NO:8), CWK, and FEHCNFNDVTTR (SEQ ID NO:9). In contrast: trypsin digestion of glycated CD59 yields only two peptides, AGLQVYNK (SEQ ID NO:8) and CWKFEHCNFNDVTTR (SEQ ID NO:10), because glycated CD59 is not cleaved and the glycated K41 site. Thus, AGLQVYNK (SEQ ID NO:8) is generated by the trypsin digestion of both glycated and non-glycated CD59, so the quantitative estimate of AGLQVYNK (SEQ ID NO:8) in a sample represents total CD59 in the sample. In contrast, the FEHCNFNDVTTR (SEQ ID NO:9) peptide is only generated by the trypsin digestion of non-glycated CD59, therefore the level of FEHCNFNDVTTR (SEQ ID NO:9) present in a digested sample can be used as a quantitative measure of the amount of non-glycated CD59 in the sample. In some embodiments, the level of CD59 in a sample can be determined using the digest methods of the invention and a comparison of the relative amounts of CWK and SEQ ID NO:10 in a digested sample.

The difference between the level (amount) of total and the amount of non-glycated CD59 is the amount of glycated CD59 in the sample. As used herein, the term "level" means amount. For example, the level of glycated CD59 in a sample is the amount of glycated CD59 in the sample. The amount can be a relative amount, or absolute amount, depending on the technique employed, as will be clear from context.

According to some aspects of the invention, agents that bind specifically to peptides generated by the digestion of glycated, non-glycated CD59, or that bind to digestion products of a fragment of CD59 [e.g. CD59$_{(29-54)}$ peptide TKAGLQVYNKCWKFEHCNFNDVTTRL (SEQ ID NO:11)] can be prepared and used to identify and quantitate the amount of glycated CD59 in a sample. As used herein, "binding specifically to" means capable of distinguishing the identified material from other materials sufficient for the purpose to which the invention relates. For example, "binding specifically to" AGLQVYNK (SEQ ID NO:8), CWK, FEHCNFNDVTTR (SEQ ID NO:9), or CWKFEHCNFNDVTTR (SEQ ID NO:10) means the ability to bind to and distinguish AGLQVYNK (SEQ ID NO:8), CWK, FEHCNFNDVTTR (SEQ ID NO:9), or CWKFEHCNFNDVTTR (SEQ ID NO:10) from each other and/or from other peptides and proteins.

Agents that bind to digestion products of glycated CD59, non-glycated CD59, or digestion products of a fragment of CD59 [e.g. CD59$_{(29-54)}$ peptide TKAGLQVYNKCWKFEHCNFNDVTTRL (SEQ ID NO:11)] include polypeptide agents. Such polypeptides include polyclonal and monoclonal antibodies, prepared according to conventional methodology.

In some embodiments, antibodies or antigen-binding fragments thereof that specifically bind to a fragment generated by digestion of a CD59 polypeptide can be used to assess the presence of glycated CD59 polypeptides in a sample. For example, an antibody or antigen-binding fragment thereof that can distinguish the fragments generated by digestion of glycated CD59 from the fragments generated by digestion of non-glycated CD59 can be used to indicate the presence and/or level of glycated CD59 in a sample.

Significantly, as is well known in the art, only a small portion of an antibody to molecule, the paratope, is involved in the binding of the antibody to its epitope (see, in general, Clark, W. R. (1986) The Experimental Foundations of Modem Immunology, Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) The Experimental Foundations of Modern Immunology, Wiley & Sons, Inc., New York; Roitt, I. (1991) Essential Immunology, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Thus, for example, PCT International Publication Number WO 92/04381 teaches the production and use of murine RSV antibodies in which at least a portion of the murine FR regions have been replaced by FR regions of human origin. Such antibodies, including fragments of intact antibodies with antigen-binding ability, are often referred to as "chimeric" antibodies. Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')2, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to digestion products of glycated CD59, non-glycated CD59, or a fragment of CD59 (glycated or non-glycated) such as $CD59_{(29-54)}$ peptide TKAGLQVYNKCWKFEHCNFNDVTTRL (SEQ ID NO:11) molecules. Thus, in some embodiments, an antibody that specifically binds to a fragment of glycated CD59 generated by enzyme digestion (e.g. trypsin digestion) and does not bind to fragments generated from a similar digestion of non-glycated CD59 can be used to determine relative amounts of glycated and non-glycated CD59 in the sample. Thus, using the differential digestion of glycated and non-glycated CD59 peptides into distinct fragments allows the determination of the presence and/or amount of glycated CD59 in a sample. One of ordinary skill will recognize that the different fragments generated by the digestion of glycated versus non-glycated CD59 peptides allow the use of binding peptides (e.g. antibodies) that specifically bind to certain fragments to determine the presence and/or amount of glycated CD59 in a sample.

These binding polypeptides may be derived also from sources other than antibody technology. For example, such polypeptide binding agents can be provided by degenerate peptide libraries that can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to a digestion product of glycated CD59, non-glycated CD59, or fragment of glycated or non-glycated CD59 [e.g. $CD59_{(29-54)}$ peptide TKAGLQVYNKCWKFEHCNFNDVTTRL (SEQ ID NO:11)] molecules. This process can be repeated through several cycles of reselection of phage that bind to a digestion product of glycated CD59, non-glycated CD59, or fragment of glycated or non-glycated CD59 [e.g. $CD59_{(29-54)}$ peptide TKAGLQVYNKCWKFEHCNFNDVTTRL (SEQ ID NO:11)] molecules. Repeated rounds lead to enrichment of phage bearing particular sequences. DNA sequences analysis can be conducted to identify the sequences of the expressed polypeptides. The minimal linear portion of the sequence that binds to a digestion product of glycated CD59, non-glycated CD59, or fragment of glycated or non-glycated CD59 [e.g. $CD59_{(29-54)}$ peptide TKAGLQVYNKCWKFEHCNFND-VTTRL (SEQ ID NO:11)] molecules can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to a digestion product of glycated CD59, non-glycated CD59, or fragment of glycated or non-glycated CD59 [e.g. $CD59_{(29-54)}$ peptide TKAGLQVYNKCWKFEHCNFNDVTTRL (SEQ ID NO:11)] molecules. Thus, digestion products of glycated CD59, non-glycated CD59, or fragment of glycated or non-glycated CD59 [e.g. $CD59_{(29-54)}$ peptide TKAGLQVYNKCWKFEHCNFNDVTTRL (SEQ ID NO:11)] molecules can be used to screen peptide libraries, including phage display libraries, to identify and select peptide binding partners of the digestion products of glycated CD59, non-glycated CD59, or fragments of glycated or non-glycated CD59 [e.g. $CD59_{(29-54)}$ peptide TKAGLQVYNKCWKFEH-CNFNDVTTRL (SEQ ID NO:11)] molecules.

As detailed herein, the foregoing antibodies and other binding molecules may be used for example to identify digestion products of glycated CD59, non-glycated CD59, or fragment of glycated or non-glycated CD59 [e.g. $CD59_{(29-54)}$ peptide TKAGLQVYNKCWKFEHCNFNDVTTRL (SEQ ID NO:11)] molecules and can be used to determine the amount of glycated CD59 in a sample. The antibodies may be coupled to specific diagnostic labeling agents for imaging of a digestion product of glycated CD59, non-glycated CD59, or fragment of glycated or non-glycated CD59 [e.g. $CD59_{(29-54)}$ peptide TKAGLQVYNKCWKFEHCNFNDVTTRL (SEQ ID NO:11)] molecules. The antibodies may also be used for immunoprecipitation, immunoblotting digestion products of glycated CD59, non-glycated CD59, or fragment of glycated or non-glycated CD59 [e.g. $CD59_{(29-54)}$ peptide TKA-GLQVYNKCWKFEHCNFNDVTTRL (SEQ ID NO:11)] molecules, using standard methods known to those of ordinary skill in the art.

The invention provides methods and kits for the determination of the fragments produced in enzymatic digests of samples that are not spiked by allowing the quantitation of one or more of the fragments that specifically represent digestion products of either CD59 that is glycated or CD59 that is not glycated. For example, in some embodiments, the presence and/or level of CWK and AGLQVYNK (SEQ ID NO:8) can be determined. The identification of a lower level of CWK than AGLQVYNK (SEQ ID NO:8) in a sample indicates that glycated CD59 was present in the sample. In some embodiments, the amount of a peptide in a digested sample is quantified. The quantitation of one or more peptides in a digested sample provides a determination of the initial amount of glycated and/or non-glycated CD59 in the sample.

The invention also involves a variety of assays based upon detecting levels of glycated CD59 in subjects. The assays include (1) characterizing the impact of blood sugar levels on glycation levels in a subject; (2) evaluating a treatment for regulating blood sugar levels in a subject; (3) selecting a treatment for regulating blood sugar levels in a subject; and (4) determining progression, progression or onset of a condition characterized by abnormal levels of glycated protein in a subject. Thus, subjects can be characterized, treatment regimens can be monitored, treatments can be selected and diseases can be better understood using the assays of the present invention. For example, the invention provides in one aspect a method for measuring the level of glycated CD59 in a subject, which is a direct indicator of the level of the subject's glycemic control. The impact of blood sugar levels or glycation levels thus can be measured due to the positive correlation between the level of circulating blood glucose and the amount of glycation of endogenous CD59. The level of glycated CD59 thus correlates with the level of glycemic control in the subject. Relatively low levels of glycated CD59 reflect well-controlled circulating blood sugar levels and selectively high levels of glycated CD59 reflect poorly controlled glycemic levels. CD59 is present in body fluids of subjects with and without diabetes. For example, the concentration of CD59 in urine is generally in a range from about 4 to 8 µg/ml of urine. In a subject with uncontrolled diabetes, the amount of the CD59 that is glycated CD59 (e.g. K41-glycated CD59) in a bodily fluid is about 50% to 60% of the CD59 present in the sample. Thus, a percentage of CD59 in a sample can be used as a determination of the glycemic status of the subject, and the percentage of glycated CD59 reflects the subject's regulation of sugar levels, e.g. the subject's level of glycemic control. A higher percentage in a sample from a subject than that found in a normal sample indicates that the subject has reduced glycemic control compared to the level of glycemic control in the subject providing the normal sample.

The assays described herein are carried out on samples. In some embodiments, a sample is a biological sample obtained from a subject. In some embodiments, a sample can be synthetic or (e.g. laboratory prepared) and not obtained from a subject. As used herein, a subject is a human, non-human primate, cow, horse, pig, dog, cat, or rodent. In all embodiments, human subjects are preferred.

As used herein, a "biological sample" encompasses a variety of sample types obtained from an individual through invasive or non-invasive approaches (e.g., urine collection, blood drawing, needle aspiration, and other procedures). The definition also includes samples that have been manipulated in any way after their procurement (through invasive or non-invasive approaches), such as by treatment with reagents, solubilization, or enrichment for certain components, such as proteins or polynucleotides. The term "biological sample" includes, but is not limited to, any body tissue or body fluid sample obtained from a subject. Body fluids include: urine, blood, saliva, lacrimal fluid, synovial fluid, cerebrospinal fluid, sweat, pulmonary secretions (sputum), seminal fluid, and feces. Preferred are body fluids, for example, lymph, saliva, blood, urine, and the like.

Particularly important subjects to which the present invention can be applied are diabetic subjects and subjects at risk for diabetes or other glucose metabolism abnormality—e.g. a subject with reduced glycemic control (ability to regulate sugar levels) compared to a normal subject.

The term "diabetic" as used herein, means an individual who, at the time the sample is taken, has a primary deficiency of insulin and/or an abnormal (e.g. reduced) ability to metabolize glucose, e.g. impaired glucose tolerance versus a normal subject. The term diabetic includes, but is not limited to, individuals with juvenile diabetes (Type 1 diabetes), adult-onset diabetes (Type 2 diabetes), gestational diabetes, and any other conditions of insulin deficiency or reduction in the ability to metabolize glucose. A subject who is an uncontrolled or not fully controlled diabetic has reduced glycemic control as compared to a subject who is not diabetic or is a controlled diabetic subject. The term "diabetic" is a term of art, known and understood by those practicing in the medical profession, a formal definition of which can be found in Harrison's Principles of Medicine (Harrisons, Vol 14, Principles of Internal Medicine, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

The assays described herein involve measuring levels of glycated CD59. Levels of glycated CD59 can be determined in a number of ways when carrying out the various methods of the invention. In one particularly important measurement, the level of glycated CD59 is measured in relation to nonglycated CD59. Thus, the measurement is a relative measure, which can be expressed, for example, as a percentage of total CD59. Another measurement of the level of glycated CD59 is a measurement of absolute levels of glycated CD59. This could be expressed, for example, in terms of grams per liter of body fluid. Another measurement of the level of glycated CD59 is a measurement of the change in the level of glycated CD59 over time. This may be expressed in an absolute amount or may be expressed in terms of a percentage increase or decrease over time.

Importantly, levels of glycated CD59 are advantageously compared to controls according to the invention. The control may be a predetermined value, which can take a variety of forms. It can be a single cut-off value, such as a median or mean. It can be established based upon comparative groups, such as in groups having normal amounts of circulating insulin and groups having abnormal amounts of circulating insulin. Another example of comparative groups would be groups having a particular disease, condition or symptoms and groups without the disease, condition or symptoms. Another comparative group would be a group with a family history of a condition and a group without such a family history. The predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk or amounts of glycated protein and the highest quadrant or quintile being individuals with the highest risk or amounts of glycated protein.

The predetermined value, of a course, will depend upon the particular population selected. For example, an apparently healthy population will have a different 'normal' range than will a population that is known to have a condition related to abnormal protein glycation. Accordingly, the predetermined value selected may take into account the category in which an individual falls. Appropriate ranges and categories can be selected with no more than routine experimentation by those of ordinary skill in the art. By abnormally high it is meant high relative to a selected control. Typically the control will be based on apparently healthy normal individuals in an appropriate age bracket.

In measuring the relative amount of glycated CD59 to nonglycated CD59, those of ordinary skill in the art will appreciate that the relative amount may be determined by measuring either the relative amount of glycated CD59 or the relative amount of nonglycated CD59. In other words, if 90% of an individual's CD59 is nonglycated CD59, then 10% of the individual's CD59 will be glycated CD59. Thus, measuring the level of glycated CD59 may be carried out by measuring the relative amount of nonglycated CD59. Similarly, when determining the level of glycated CD59 in a sample using the mass spectrometric or other peptide identification method of the invention, the difference between the total amount of CD59 and the amount of non-glycated CD59 after digestion of the spiked sample is the amount of glycated CD59 in the sample.

It will also be understood that the controls according to the invention may be, in addition to predetermined values, samples of materials tested in parallel with the experimental materials. Examples include samples from control populations or control samples generated through manufacture to be tested in parallel with the experimental samples.

In some embodiments of the invention, methods provided are used to determine the level of glycated CD59 is a subject at risk of having a diabetic disorder, or blood sugar regulation disorder. As used herein, a subject "at risk" is a subject who is considered more likely to develop a disease state or a physiological state than a subject who is not at risk. A subject "at risk" may or may not have detectable symptoms indicative of the disease or physiological condition, and may or may not have displayed detectable disease prior to the treatment methods (e.g., therapeutic intervention) described herein. "At risk" denotes that a subject has one or more so-called risk factors. A subject having one or more of these risk factors has a higher probability of developing one or more disease(s) or physiological condition(s) than a subject without these risk factor(s). These risk factors can include, but are not limited to, history of family members developing one or more diseases (e.g. diabetes), related conditions (e.g. pregnancy), or pathologies, history of previous disease, age, sex, race, diet, presence of precursor disease, genetic (i.e., hereditary) considerations, and environmental exposure. The level of risk can be assessed using standard methods known to those in the art. For example, based on factors such as medical history, family medical history, and current medical condition, a health care professional may assess a percentage chance that a subject will have or will develop a diabetic disorder or blood sugar regulation disorder. For example, a health care professional may determine that a subject who had gestational diabetes or borderline gestational diabetes may have a 20%, 30%, 40%, 50%, 60%, 70% or more chance of developing gestational diabetes in a subsequent pregnancy. Those of skill in the art will recognize that a subject's level of risk for other diabetic disorders or blood sugar regulation disorders can also be evaluated using standard methods.

As mentioned above, it is also possible to characterize blood sugar levels by monitoring changes in the absolute or relative amounts of glycated CD59 over time. For example, it is expected that an increase in glycated CD59 correlates with increasing dysregulation of glycemic levels. Accordingly one can monitor glycated CD59 levels over time to determine if glycemic levels of a subject are changing. Changes in relative or absolute glycated CD59 of greater than 0.1% may indicate an abnormality. Preferably, the change in glycated CD59 levels, which indicates an abnormality, is greater than 0.2%, greater than 0.5%, greater than 1.0%, 2.0%, 3.0%, 4.0%, 5.0%, 7.0%, 10%, 15%, 20%, 25%, 30%, 40%, 50%, or more. Reductions in amounts of glycated CD59 over time may indicate improved glycemic control. For example, reductions in the amount of glycated CD59 of greater than 0.2%, greater than 0.5%, greater than 1.0%, 2.0%, 3.0%, 4.0%, 5.0%, 7.0%, 10%, 15%, 20%, 25%, 30%, 40%, 50%, or more indicate increased glycemic control in a subject.

The invention in another aspect provides a diagnostic method to determine the effectiveness of treatments for abnormal glycemic levels. The "evaluation of treatment" as used herein, means the comparison of a subject's levels of glycated CD59 measured in samples collected from the subject at different sample times, preferably at least one day apart. The preferred time to obtain the second sample from the subject is at least one day after obtaining the first sample, which means the second sample is obtained at any time following the day of the first sample collection, preferably at least 12, 18, 24, 36, 48 or more hours or days after the time of first sample collection. In some embodiments the time between sample collections is about 1, 2, 3, 4, 5, 6, 7, 8, 9, 10, 11 or more hours.

The comparison of levels of glycated CD59 in two or more samples, taken at different times, or on different days, is a measure of level of the subject's glycemic control and allows evaluation of the treatment to regulate blood sugar levels. The comparison of a subject's levels of glycated CD59 measured in samples obtained at different times or on different days provides a measure of glycemic control to determine the effectiveness of any treatment to regulate blood sugar levels.

As will be appreciated by those of ordinary skill in the art, the evaluation of the treatment also may be based upon an evaluation of the symptoms or clinical end points of the associated disease, such as the vascular complications of diabetes. Thus, the methods of the invention also provide for determining the onset, progression, and/or regression of a condition which is characterized by abnormal levels of glycated protein, including those characterized by abnormal levels of glycated CD59. In some instances, the subjects to which the methods of the invention are applied are already diagnosed as having a particular condition or disease. In other instances, the measurement will represent the diagnosis of the condition or disease. In some instances, the subjects will already be undergoing drug therapy for regulating blood sugar levels, while in other instances the subjects will be without present drug therapy for regulating blood sugar levels.

According to still another aspect of the invention, a method is provided for treating a subject to reduce the risk of a disorder associated with abnormally high levels of glycated CD59. The method involves selecting and administering to a subject who is known to have an abnormally high level of glycated CD59, an agent for treating the disorder. Preferably, the agent is an agent for reducing glycated CD59 levels and is administered in an amount effective to reduce glycated CD59 levels.

In this aspect of the invention, the treatments are based upon selecting (e.g. identifying) subjects who have unwanted, elevated levels of glycated CD59. Such subjects may already be receiving a drug for regulating blood sugar levels, but using the methods of the invention, are now identified as candidates for an elevated level of the drug based upon the presence of the elevated levels of glycated CD59. It may be appropriate according to the invention to alter a therapeutic regimen for a subject, based upon the measurement of the level of glycated CD59. This can be understood in connection with treatment of diabetics.

Diabetics are treated in at least three different ways. Some diabetics are treated only with non-drug therapy, such as exercise and diet. Other diabetics are treated with oral drug therapy, but not with insulin that is injected. Finally, some diabetics are treated with insulin or analogs of insulin by injection. According to the present invention, as a result of determining an elevated level of glycated CD59, an individual undergoing only non-drug therapy may be a candidate for drug therapy as a result of the glycated CD59 test. Likewise, a subject receiving only oral drug therapy may be a candidate for an insulin-based injectable therapy, due to the glycated CD59 test. Finally, a subject may be free of any present treatment but may be a candidate for blood sugar level regulating treatment as a result of the glycated CD59 test. Thus, subjects may be selected (e.g. identified) and treated with elevated levels of the same drugs or with different therapies as a result of the assays of the invention.

According to the present invention, some of the subjects are free of symptoms otherwise calling for treatment with a particular therapy. This means that absent the glycated CD59 test, the subject would not according to convention as of the date of the filing of the present application have symptoms calling for treatment with a particular therapy. It is only as a result of the measuring the level of glycated CD59 that the subject becomes a candidate for treatment with the therapy.

Drug therapies for regulating blood sugar levels include oral therapies with hypoglycemic agents and/or oral antidiabetic agents, injectable therapies, and the like. Non-drug therapies for regulating blood sugar level include, but are not limited to, diatetic and/or exercise control measures.

Diet and exercise alterations include, but are not limited to, reducing caloric intake, and/or increasing fiber intake, and/or decreasing fat intake, and/or increasing exercise level.

Oral drug therapies for regulating blood sugar levels include hypoglycemic agents that may include, but are not limited to:

Acarbose; Acetohexamide; Chlorpropamide; Darglitazone Sodium: Glimepiride; Glipizide; Glyburide, Repaglinide; Troglitazone; Tolazamide; Tolbutamide.

Oral drug therapies for regulating blood sugar levels include antidiabetic agents that may include but are not limited to: Acarbose, Acetohexamide; Buformin; Butoxamine Hydrochloride; Camiglibose; Chlorpropamide; Ciglitazone; Englitazone Sodium; Etoformin Hydrochloride; Gliamilide; Glibornuride; Glicetanile, Gliclazide Sodium; Gliflumide; Glipizide; Glucagon; Glyburide; Glyhexamide; Glymidine Sodium; Glyoctamide; Glyparamide; Insulin; Insulin, Dalanated; Insulin Human; Insulin Human, Isophane; Insulin Human Zinc; Insulin Human Zinc, Extended; Insulin, Isophane; Insulin Lispro; Insulin, Neutral; Insulin Zinc; Insulin Zinc, Extended; Insulin Zinc, Prompt; Linogliride; Linogliride Fumarate; Metformin; Methyl Palmoxirate; Palmoxirate Sodium; Pioglitazone Hydrochloride; Pirogliride Tartrate; Proinsulin Human; Repaglinide; Seglitide Acetate; Tolazamide; Tolbutamide; Tolpyrramide; Troglitazone; Zopolrestat.

Injectable therapies for regulating blood sugar levels include, but are not limited to: Fast-Acting Insulin:

Insulin Injection: regular insulin; Prompt Insulin Zinc Suspension; Semilente® insulin. These categories include preparations such as: Humalog® Injection; Humulin® R; Iletin II; Novolin R, Purified Pork Regular Insulin; Velosulin BR Human Insulin Intermediate-acting Insulin:

Isophane Insulin Suspension: NPH insulin, isophane insulin; Insulin Zinc Suspension Lente® Insulin. These categories include preparations such as: Humulin® L; Humulin® R; Humulin® N NPH; Iletin® II, Lente®; Iletin® II, NPH; Novolin® L, Novolin® N, Purified Pork Lente® insulin, Purified Pork NPH isophane insulin. Intermediate and Rapid-acting Insulin Combinations:

Human Insulin Isophane Suspension/Human Insulin Injection;. This category includes preparations such as: Humulin® 50/50; Humulin®70/30; Novolin®70/30 Long-acting Insulin: Protamine Zinc Insulin Suspension; Extended Insulin Zinc Suspension. These categories include preparations such as: Ultralente® Insulin, Humulin® U.

Reducing the risk of a disorder associated with abnormally high levels of glycated CD59 means using treatments and/or medications to reduce glycated CD59 levels, therein reducing, for example, the subject's risk of vascular complications including but not limited to: diabetic nephropathy, diabetic retinopathy, macro-vascular disease, micro-vascular disease, and diabetic neuropathy.

In a subject determined to have an abnormally high level of glycated CD59, an effective amount is that amount effective to reduce glycated CD59 levels in the subject. A response can, for example, also be measured by determining the physiological effects of the hypoglycemic, antidiabetic, or insulin composition, such as the decrease of disease symptoms following administration of the hypoglycemic, antidiabetic, or insulin. Other assays will be known to one of ordinary skill in the art and can be employed for measuring the level of the response. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormally elevated levels of glycated CD59.

An "effective amount" of a drug therapy is that amount of a hypoglycemic, antidiabetic, or insulin or insulin analog that alone, or together with further doses, produces the desired response, e.g. reduction of glycemic level or glycated CD59 levels.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the hypoglycemic, antidiabetic, or insulin composition (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of hypoglycemic, antidiabetic, or insulin for producing the desired response in a unit of weight or volume suitable for administration to a patient.

The doses of hypoglycemic, antidiabetic, or insulin administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Various modes of administration will be known to one of ordinary skill in the art which effectively deliver the hypoglycemic, antidiabetic, or insulin to a desired tissue, cell or bodily fluid. Preferred methods for administering the hypoglycemic and antidiabetic are oral. The preferred method of administering insulin is by injection. Administration includes: topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences*, 18th edition, 1990) provide modes of administration and formulations for delivery of various pharmaceutical preparations and formulations in pharmaceutical carriers. Other protocols which are useful for the administration of hypoglycemic, antidiabetic, or insulin will be known to one of ordinary skill in the art, in which the dose amount, schedule of administration, sites of administration, mode of administration (e.g., intra-organ) and the like vary from those presented herein.

Administration of hypoglycemic, antidiabetic, or insulin to mammals other than humans, e.g. for testing purposes or veterinary therapeutic purposes, is carried out under substantially the same conditions as described above. It will be understood by one of ordinary skill in the art that this invention is applicable to both human and animal diseases which can be treated by hypoglycemic, antidiabetic or insulin. Thus, this invention is intended to be used for diagnostics and therapeutics in husbandry and veterinary medicine as well as for human diagnostics and therapeutics.

When administered, the pharmaceutical preparations of the invention are applied in pharmaceutically acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts. Preferred components of the composition are described above in conjunction with the description of the hypoglycemic, antidiabetic, or insulin compositions of the invention.

A hypoglycemic, antidiabetic, or insulin composition may be combined, if desired, with a pharmaceutically-acceptable carrier. The term "pharmaceutically acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the hypoglycemic, antidiabetic, or insulin, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise hypoglycemid, antidiabetic, or insulin. This preparation may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

The application of the invention to a diabetic subject under treatment with an oral blood sugar regulating agent and otherwise free of symptoms calling for any oral blood sugar regulating agent, as used herein means a subject treated with oral blood sugar regulators whose glycemic-control levels appear normal based on standard diagnostic criteria, including but not limited to measurement of glycated hemoglobin levels.

The application of the invention to a diabetic subject under treatment with insulin (including analogs thereof) and otherwise free of symptoms calling for any insulin, as used herein means a subject treated with insulin whose glycemic-control levels appear to be normal based on standard diagnostic criteria, including but not limited to measurement of glycated hemoglobin levels.

Dosages of blood sugar regulating agents are well-known to those of ordinary skill in the art and documented in the literature.

Also within the scope of the invention are kits comprising the compositions of the invention and instructions for use. The kits can further contain at least one additional reagent, such as a control sample. Kits of the invention can be prepared for in vitro diagnosis, prognosis and/or monitoring a diabetic condition, blood sugar regulating disorder, or complication by the mass spectrometry and other detection methods described above. Kits of the invention may include a CD59 peptide and the CD59 peptide may be a native or labeled CD59 peptide.

For example, kits containing a $CD59_{(29-54)}$ peptide TKAGLQVYNKCWKFEHCNFNDVTTRL; (SEQ ID NO:5) that includes deuterated-$(d_8)$-$V_{(35)}$ and $d_8$-$F_{(47)}$ can be prepared. The components of the kits can be packaged either in aqueous medium or in lyophilized form. A kit of the invention, in some embodiments, may further comprise a container containing glycated CD59 molecule, which may be K41 glycated CD59 and/or a container containing non-glycated CD59 or non-K41 glycated CD59. Some or all of the kit components may be frozen.

A kit of the invention may also include a container containing an enzyme, for example, trypsin. The enzyme may be in lyophilized form or may be in aqueous medium. The kit may also include the solution for reconstitution of the enzyme. A kit of the invention may also include control compounds and solutions for testing the activity of the enzyme, for example materials to perform an enzymatic assay of trypsin. Such materials may include, buffer, a non-limiting example of which is sodium phosphate buffer, Nα-Benzoyl-L-Arginine Ethyl Ester Solution (BAEE), HCl or other acid and trypsin. A kit may also include instructions for determining the activity of the enzyme per unit of the enzyme.

A kit of the invention may comprise a carrier being compartmentalized to receive in close confinement therein one or more container means or series of container means such as test tubes, vials, flasks, bottles, syringes, or the like. A first of said container means or series of container means may contain a CD59 peptide, such as, but not limited to, $CD59_{(29-54)}$ peptide TKAGLQVYNKCWKFEHCNFNDVTTRL (SEQ ID NO:5) that includes to deuterated-$(d_8)$-$V_{(35)}$ and $d_8$-$F_{(47)}$. A second container means or series of container means may contain glycated CD59 and/or non-glycated CD59. A third container may include the enzyme, e.g. trypsin. In some embodiments, the kit may include one or more solutions or molecules that can be used to make a labeled CD59 peptide. An example of a labeled CD59 peptide, though not intended to be limiting, is CD59 peptide that is deuterated-$(d_8)$ at $V_{(35)}$ and $F_{(47)}$ (corresponding to the residues of mature CD59). A kit of the invention may also include a native (unlabeled) CD59 peptide. For example, a kit of the invention may include native $CD59_{(29-54)}$ peptide TKAGLQVYNKCWKFEHCNFNDVTTRL (SEQ ID NO:11), or other native CD59 peptide. One of ordinary skill in the art will recognize that in addition to deuterated peptides, peptides of the kits may be labeled with other types of labels and the kits may include additional types of labeling compounds.

A kit of the invention may also include an antibody that specifically binds to a CD59 peptide. For example, a kit may include an antibody that specifically recognizes a trypsin digest fragment of CD59. Such an antibody can be used to detect the presence of digest fragments using the methods provided herein, thus allowing the determination of the presence and/or level of glycated CD59 in a sample.

A kit of the invention may also include vials, cuvettes, pipet tips, transfer pipets, solutes, sterile and/or distilled water, one or more control samples, (e.g. blank control, test control), printed graphs, tables, figures, or diagrams, which may be used for interpretation and/or analysis of results or for instructional purposes.

A kit of the invention may also include equipment and/or supplies for mass spectrometric or other methods of determining the level of glycated CD59. For example, a kit may include ELISA assay materials, gel preparation materials (e.g. solutions, agarose, acrylamide, control markers, dyes and/or labels, etc,). A kit may also include materials for chromatographic analysis, e.g. beads, solvents, solutes, control samples etc, columns, etc.

In some embodiments, materials for analysis of the level of glycated CD59 are provided in a ready-to-use format. In other embodiments, the kits provide materials that can be utilized for determining the level of glycated CD59 in a sample and will be assembled for use by the operator. Some kits of the invention will include all materials necessary for determining the level of glycated CD59 in a sample, and other kits of the invention will include some, but not all of the materials for the determination of the level of CD59 in a sample. In the latter case, additional materials will be provided by the operator and may include: gas chromatographs, mass spectrophotometers, pipets, tubes, gel apparatus, flasks, solutions, enzymes, CD59, etc.

Referring to FIG. 1, a kit according to the invention is shown. The kit 11 includes a package 15 housing a container 17 which contains an agent for determining the level of glycated CD59 in a sample. The kit also includes a control 19. The kit also may further comprise instructions 21, as described above. The instructions typically will be in written form and will provide guidance for carrying-out the assay embodied by the kit and for making a determination based upon that assay.

Examples

Introduction

Mass spectrometry is a highly accurate and reproducible method that is currently being used to quantitate small molecules in plasma and urine samples. This methodology allows the analysis of a large number of samples in high throughput mode. The relative high levels of soluble CD59 in urine (5 µg/ml) and plasma (15-20 ng/ml) favor the feasibility of this approach. Trypsin hydrolyzes peptide bonds on the N-terminus of positively charged amino acids such as K and R. Our studies confirmed that modifications such as glycation of the amino acid side chain changed the trypsin peptide map of proteins, hence, glycated K41 on CD59 is no longer recognized as a trypsin cut site.

Methods

For mass spectrometry analysis, we have synthesized the $CD59_{(29-54)}$ peptide TKAGLQVYNKCWK*FEHCNFNDVTTRL (SEQ ID NO:5) with deuterated-($d_8$)-$V_{(35)}$ and $d_8$-$F_{(47)}$. A known amount of this peptide was added as an internal standard to each sample prior to trypsinization. The spiked samples were then trypsinized for 30 minutes at 37° C. Trypsinization of the urine or plasma sample with the added internal standard $d_8$-$CD59_{(29-54)}$ peptide yielded the following peptides:

TABLE 1

Trypsin products of non-glycated CD59.

| Trypsin products of non-glycated CD59 | Trypsin products of $CD59_{(29-54)}$ peptide |
|---|---|
| AGLQVYNK (SEQ ID NO: 8) | $AGLQV_{d8}YNK$ (SEQ ID NO: 6) |
| CWK | CWK |
| FEHCNFNDVTTR (SEQ ID NO: 9) | $FEHCNF_{d8}NDVTTR$ (SEQ ID NO: 7) |

In contrast: trypsin digestion of glycated CD59 yielded only two peptides because glycated CD59 is not cleaved at the glycated K41 site (*=K41 site).

TABLE 2

Trypsin products of glycated CD59

Trypsin products of glycated CD59

AGLQVYNK (SEQ ID NO: 8)
CWKFEHCNFNDVTTR (SEQ ID NO: 10)

Because isotopically labeled and natural peptides ionize in an identical manner, the ionization of the internal standard peptides [$AGLQV_{d8}YNK$ (SEQ ID NO:6) and $FEHCNF_{d8}NDVTTR$ (SEQ ID NO:7)] was identical to the ionization of the peptides derived from the subject's CD59 [AGLQVYNK (SEQ ID NO:8) and FEHCNFNDVTTR (SEQ ID NO:9)]. Thus, peptides derived from either the internal standard or the subject's CD59 have identical charge but a different mass of 8 units that allows their unambiguous identification and quantitation provided that the amount of the labeled $CD59_{(29-54)}$ peptide added to the sample was known. The mass difference of 8 is the result of the presence of $V_{d8}$ in $AGLQV_{d8}YNK$ (SEQ ID NO:6) and of $F_{d8}$ in $FEHCNF_{d8}NDVTTR$ (SEQ ID NO:7).

The AGLQVYNK (SEQ ID NO:8) peptide was generated by the trypsin digestion of both glycated and non-glycated CD59. Thus, the quantitative estimate of AGLQVYNK (SEQ ID NO:8) represented total CD59 in the sample. In contrast, the FEHCNFNDVTTR (SEQ ID NO:9) peptide was only generated by the trypsin digestion of non-glycated CD59. Thus, the quantitative estimate of FEHCNFNDVTTR (SEQ ID NO:9) represented non-glycated CD59 in the sample. The difference between total and non-glycated CD59 represented the amount of glycated CD59.

This method was less cumbersome and more accurate than the standard ELISA and thus allows processing of hundreds of samples per day.

Results

Progress on the use of isotope ration mass spectrometry for the quantitation of CD59 and glycated CD59.

Figure 2:
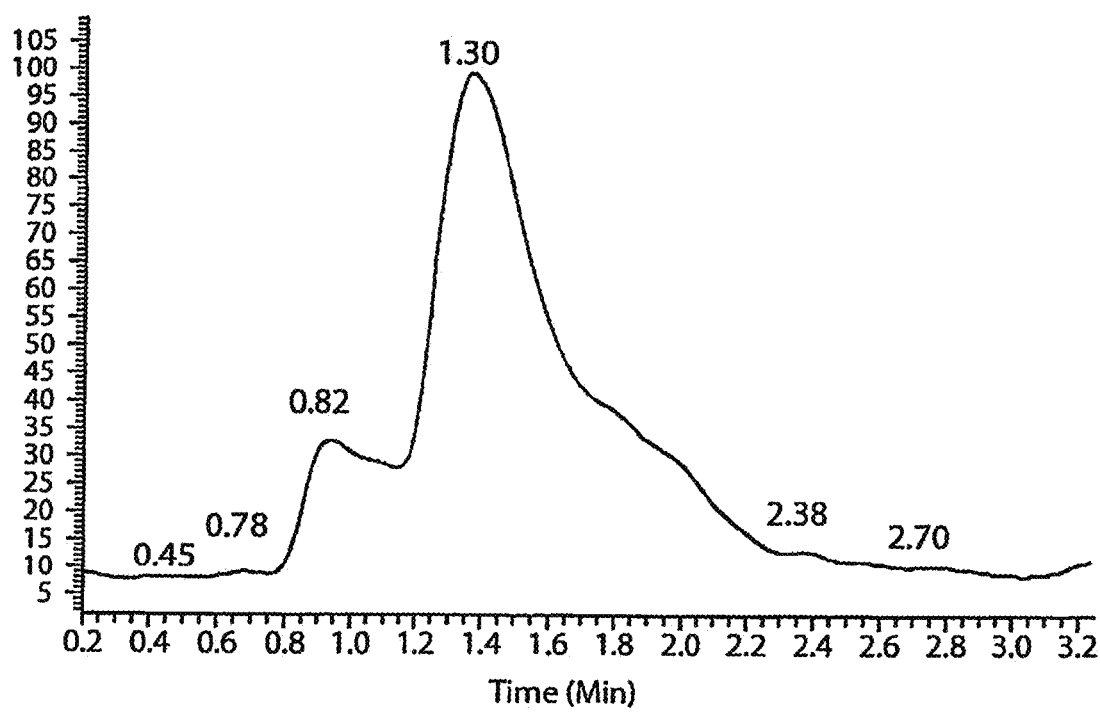
FIG. 2 is a graph of the total ion current of the peptide.

1) The LCQ Advantage with an APCI probe was switched over to the ESI probe and tuned on MRFA.
2) The instrument was tuned and a tune file was created using the tryptic digest of the isotopically labeled peptide TKAGLQVYNKCWKFEHCNFNDVTTRL (SEQ ID NO: 5).
3) a test run was performed on the LCMS on the tryptic digested peptide using the Biobasic 100 column for the LC. FIG. 2 is a graph of the total ion current of the peptide.

Figure 3:
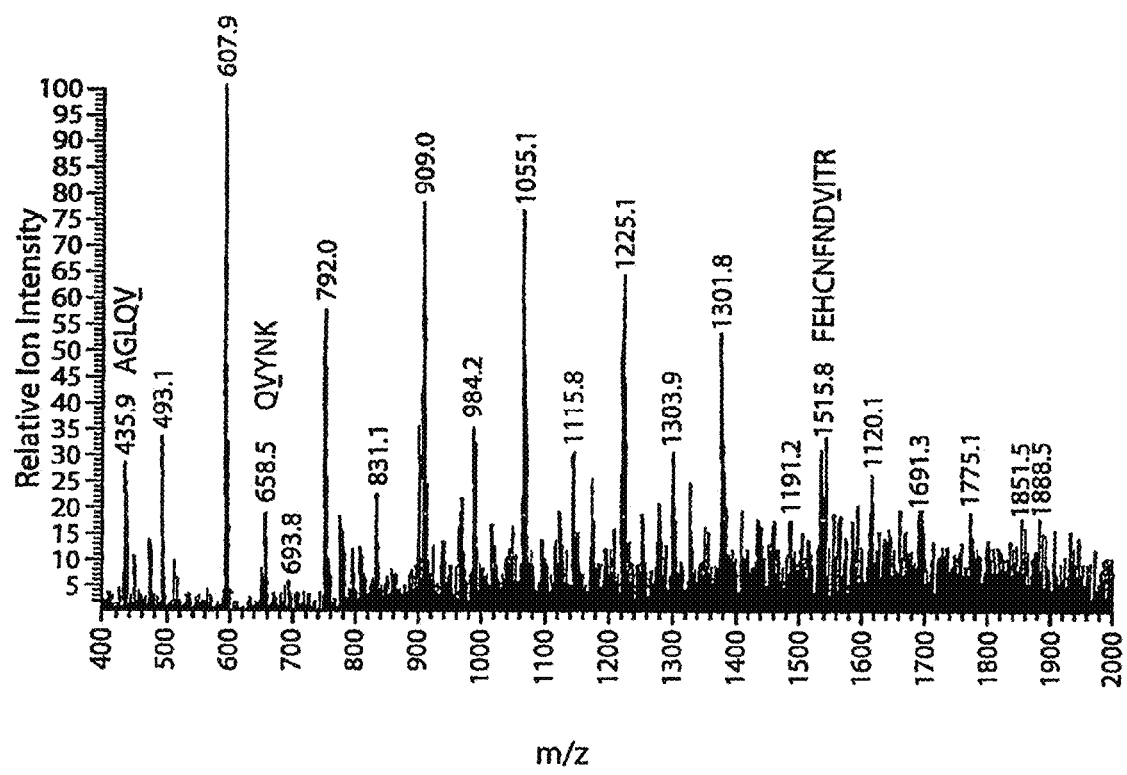
FIG. 3 is a mass spectrometry profile showing the peptides of interest. (AGLQV is SEQ ID NO:12; QVYNK is SEQ ID NO:13; and FEHCNFNDVTTR is SEQ ID NO:9).

FIG. 3 is the mass spectrometry profile showing the peptides of interest. (AGLQV is SEQ ID NO:12; QVYNK is SEQ ID NO:13; and FEHCNFNDVTTR is SEQ ID NO:9).

Although the invention has been described in detail for the purpose of illustration, it is understood that such detail is solely for that purpose and variations can be made by those skilled in the art without departing from the spirit and scope of the invention which is defined by the following claims.

The contents of all references, patents, patent documents, and published patent applications cited throughout this application are incorporated herein by reference in their entirety.

The invention claimed is:

1. A composition comprising:
an isolated peptide consisting of an amino acid sequence set forth as AGLQVYNKCWKFEHCNFNDVTTR (SEQ ID NO:15), or TKAGLQVYNKCWKFEHCNFNDVTTRL (SEQ ID NO: 11) wherein the sequence is labeled with one or more labels.

2. The composition of claim 1, wherein the label is selected from the group consisting of stable isotopes, fluorescent labels, radiolabels, enzyme labels, and luminescent labels.

3. The composition of claim 1, wherein the one or more labels are at one or more peptide that correspond to residues A31, G32, L33, Q34, V35, Y36, N37, K38, C39, W40, K41, F42, E43, H44, C45, N46, F47, N48, D49, V50, T51, T52, or R53 of mature CD59 peptide.

4. The composition of claim 1, wherein the one or more labels is on one or more amino acids of the portion of the sequence set forth as SEQ ID NO:15 that is AGLQVYNK (SEQ ID NO:8).

5. The composition of claim 1, wherein the one or more labels is on one or more amino acids of the portion of the sequence set forth as SEQ ID NO:15 that is CWKFEHCNFNDVTTR (SEQ ID NO:10).

6. The composition of claim 1, wherein the one or more labels is on one or more amino acids of the portion of the sequence set forth as SEQ ID NO:15 that is CWK.

7. The composition of claim 1, wherein the one or more labels is on one or more amino acids of the portion of the sequence set forth as SEQ ID NO:15 that is FEHCNFNDVTTR (SEQ ID NO:9).

8. The composition of claim 1, wherein the label is at the residue that corresponds to residue N37 and/or F47 of mature CD59 peptide.

9. The composition of claim 8, wherein the peptide has the amino acid sequence
AGLQV$_{d8}$YNKCWKFEHCNF$_{d8}$NDVTTR (SEQ ID NO:17).

10. The composition of claim 8, wherein the peptide has the amino acid sequence
AGLQV$_{d8}$YNKCWKFEHCNF$_{d8}$NDVTTRL (SEQ ID NO:16).

11. The composition of claim 8, wherein the labeled peptide is TKAGLQV$_{d8}$YNKCWKFEHCNF$_{d8}$NDVTTRL (SEQ ID NO:5).

* * * * *